(12) United States Patent
Ohkubo et al.

(10) Patent No.: US 6,736,798 B2
(45) Date of Patent: May 18, 2004

(54) NEEDLE GUARD AND CAPPED NEEDLE GUARD AND GUARDED WINGED NEEDLE ASSEMBLY

(75) Inventors: Masato Ohkubo, Tokyo (JP); Kei Abe, Tokyo (JP); Seiichi Ono, Oita (JP)

(73) Assignee: Kawasumi Laboratories, Inc., Tokyo (JP)

( * ) Notice: Subject to any disclaimer, the term of this patent is extended or adjusted under 35 U.S.C. 154(b) by 0 days.

(21) Appl. No.: 10/354,199

(22) Filed: Jan. 30, 2003

(65) Prior Publication Data

US 2004/0019334 A1 Jan. 29, 2004

(30) Foreign Application Priority Data

Jul. 26, 2002 (JP) ........................................ 2002-217790

(51) Int. Cl.⁷ ................................................ A61M 5/00
(52) U.S. Cl. ........................ 604/177; 604/110; 604/263
(58) Field of Search ............................ 604/164.08, 192, 604/198, 263, 171, 177, 110, 197

(56) References Cited

U.S. PATENT DOCUMENTS

| 5,169,392 A | * | 12/1992 | Ranford et al. | 604/198 |
| 6,017,329 A | * | 1/2000 | Hake | 604/198 |
| 2002/0099340 A1 | * | 7/2002 | Crawford et al. | 604/263 |
| 2003/0055381 A1 | * | 3/2003 | Wilkinson | 604/177 |

* cited by examiner

*Primary Examiner*—Brian L. Casler
*Assistant Examiner*—Lina R Kontos
(74) *Attorney, Agent, or Firm*—Oblon, Spivak, McClelland, Maier & Neustadt, P.C.

(57) ABSTRACT

A cylindrical needle guard for attaching and protecting a medical winged needle assembly to which a tube is connected, comprising at least two or more projecting portions on the top sidewall from the front portion to the rear portion, a slit at the bottom of the rear portion along a longitudinal direction of the needle guard, and a groove to fix the tube on the top sidewall of the rear portion; or comprising a pair of stoppers on both sides of the body and locking portions at thick portions and at the bottom of the stoppers for locking the wings of the winged needle assembly. This winged needle assembly to which the tube is connected is safely and securely retracted and locked in the needle guard.

25 Claims, 22 Drawing Sheets

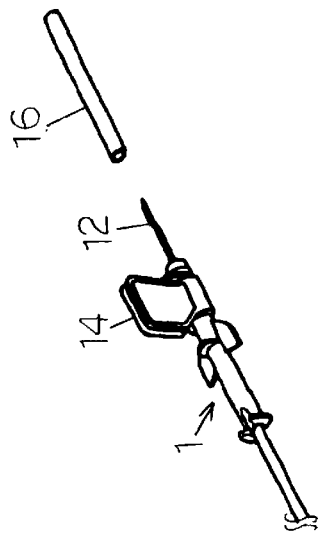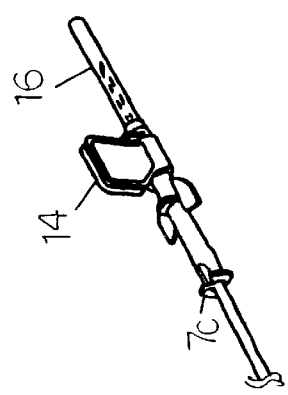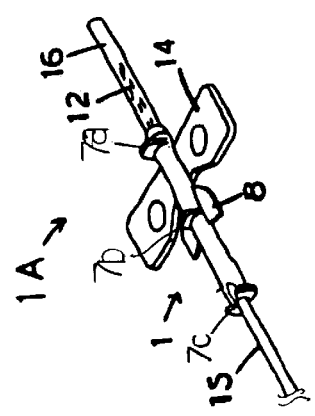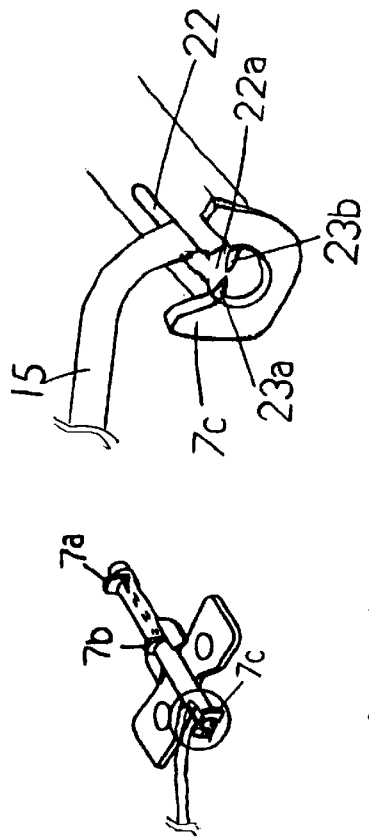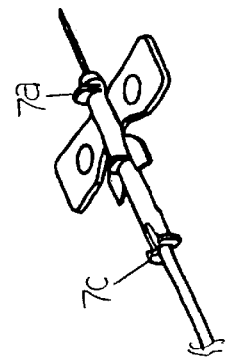

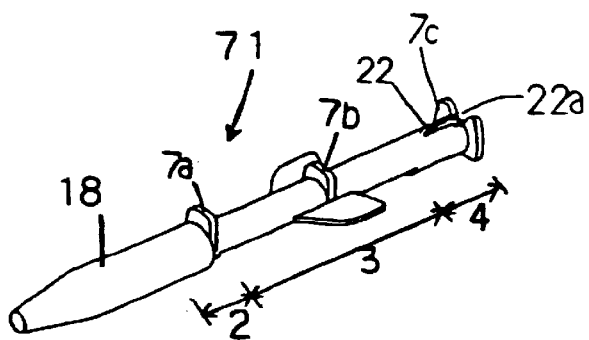
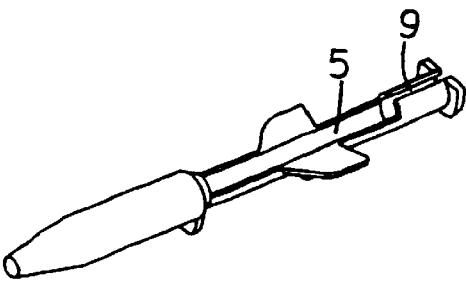
Fig.4a                Fig.4b
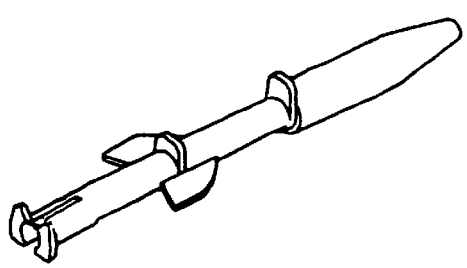
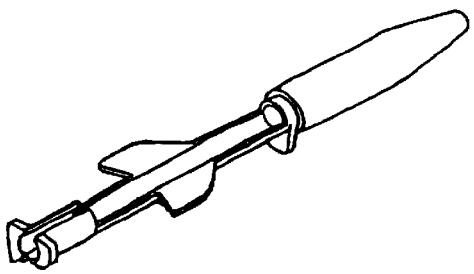
Fig.4c                Fig.4d

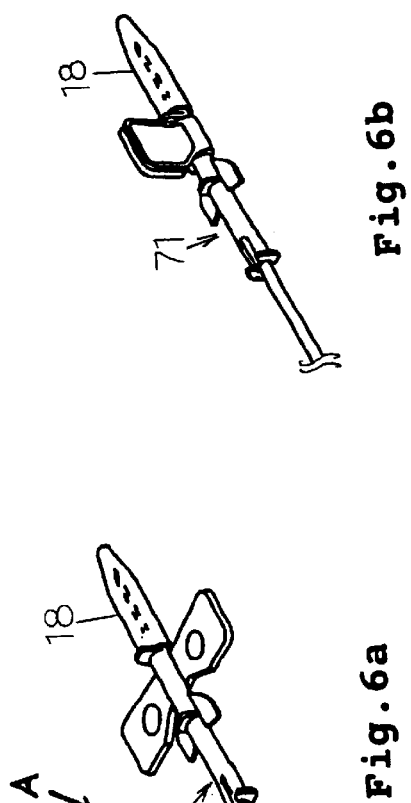
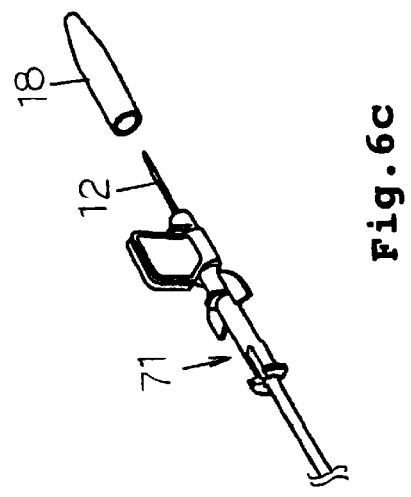
Fig.6a
Fig.6b
Fig.6c
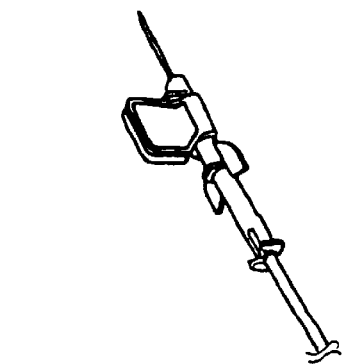
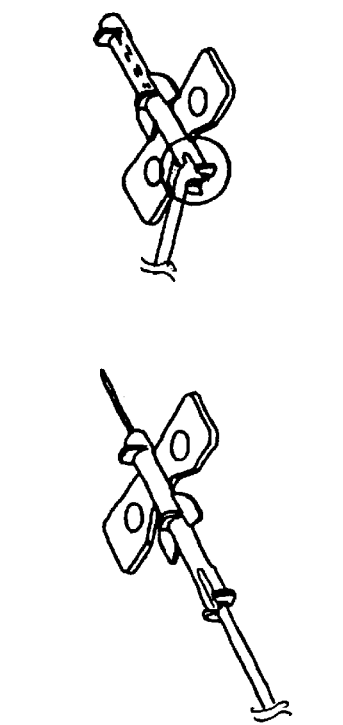
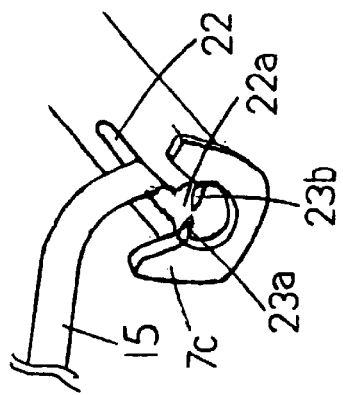
Fig.6d
Fig.6e
Fig.6f
Fig.6f1

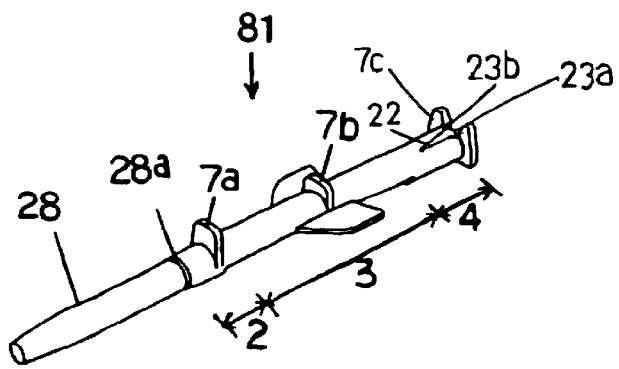
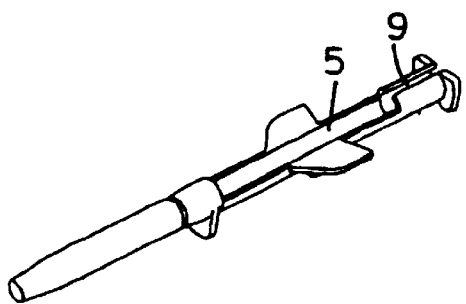
Fig.7a  Fig.7b
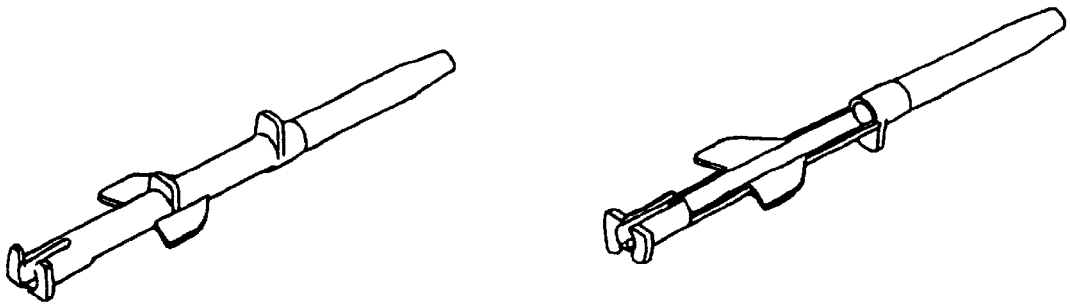
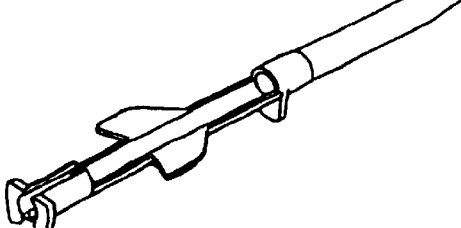
Fig.7c  Fig.7d

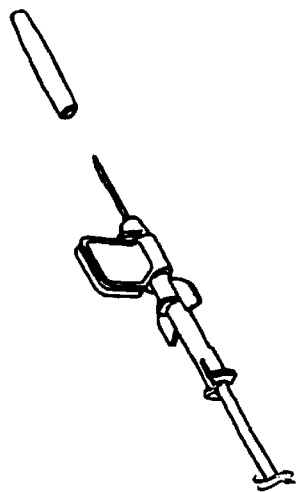
Fig. 9c
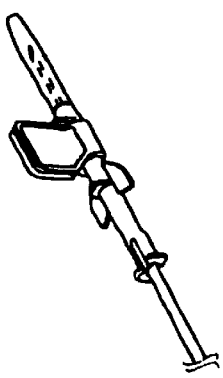
Fig. 9b
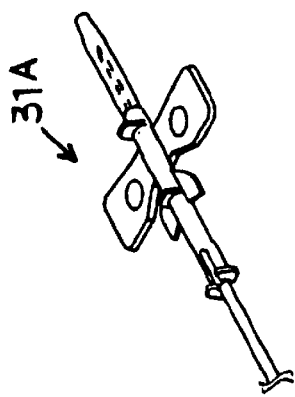
Fig. 9a
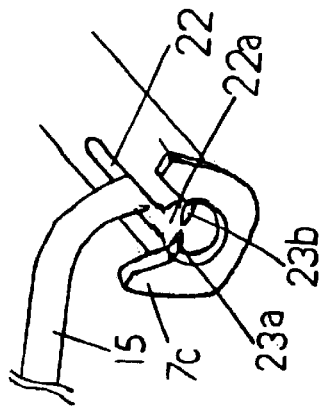
Fig. 9f1
Fig. 9f
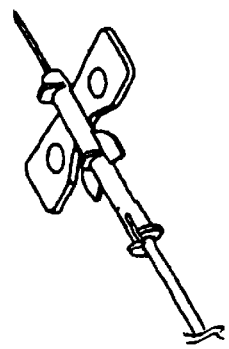
Fig. 9e
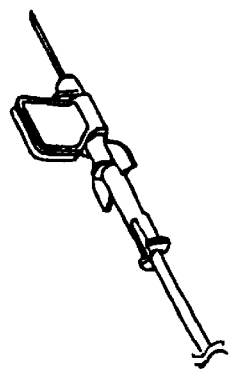
Fig. 9d

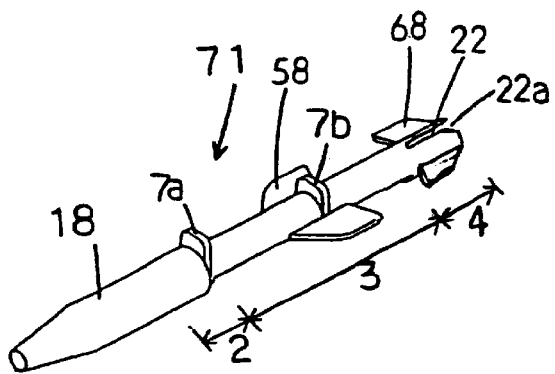
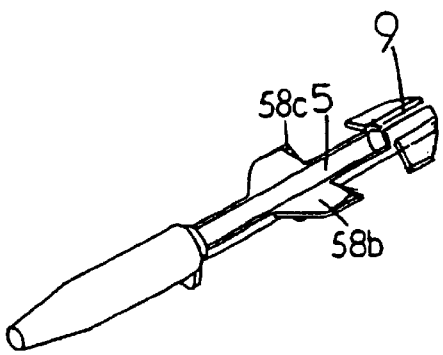
Fig.16a    Fig.16b
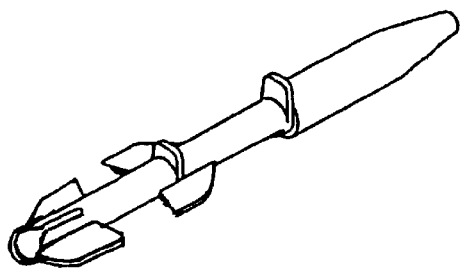
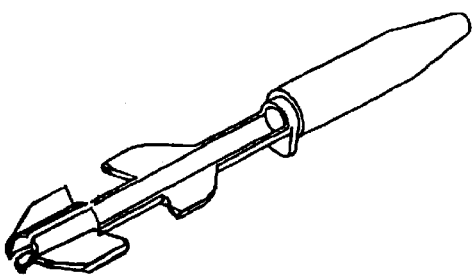
Fig.16c    Fig.16d

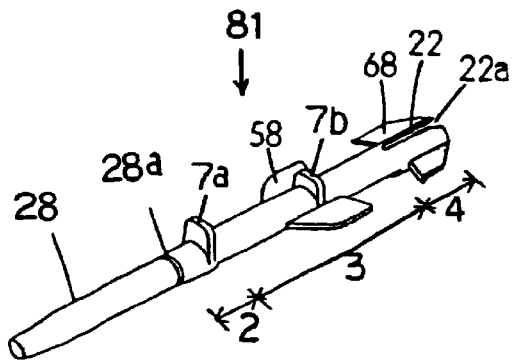
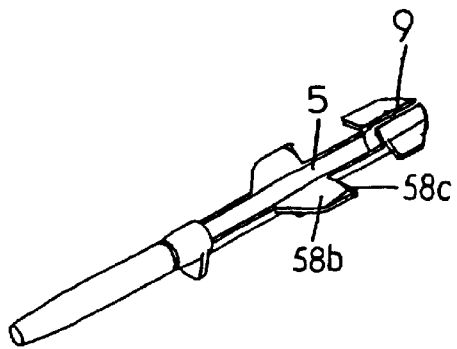
Fig.19a                    Fig.19b
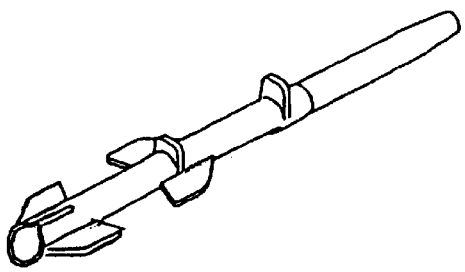
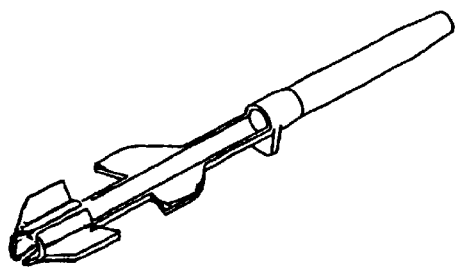
Fig.19c                    Fig.19d

NEEDLE GUARD AND CAPPED NEEDLE GUARD AND GUARDED WINGED NEEDLE ASSEMBLY

BACKGROUND OF THE INVENTION

1. Field of the Invention

This invention relates to an improvement of a needle guard, a capped needle guard, and a guarded winged needle assembly for attaching and protecting a winged needle assembly such as PSV (Pediatric Scalp Vein) or AFV (Arteriovenous Fistula) used for dialysis, fluid and/or blood infusion, and so on, and an improvement of protection ability, stability, and operationality of the above-mentioned needle assembly.

2. Description of the Related Art

With the rapid spread of infectious diseases such as viral hepatitis and AIDS through infected medical needles used for carriers' blood and/or fluid infusion, the greatest care must be given in medical facilities to avoid infection from accidental needle sticks by workers engaged in blood infusion and dialysis and to protect environmental pollution by infected and contaminated needle disposal.

For example, cylindrical or tapered caps for winged needle assemblies or medical needles for blood collection are used for protection of needle tips when stored. These caps are also used for safety when discarding needles after use. However, these needles with blood are so extra-fine that accidental needle sticks by workers trying to attach such caps and needles with their hands often happen due to fine visual errors. Meanwhile, disposal of needles without such caps induces a great risk of accidental needle sticks with contaminated blood by waste disposal workers. These practices are not acceptable.

As a result, different types of needle guards to securely retract medical needles after use are suggested. They are normally cylindrical and retract needles by sliding needles in the needle guards. They are composed in the way that needles can be both exposed and retracted by sliding. These guards for winged needle assemblies should be especially composed in the way that wings do not interfere slides of the needle guards.

U.S. Patent Numbers given to Utterberg U.S. Pat. Nos. 5,112,311, 5,433,703, 5,562,636 and 5,562,637 are the examples of such needle guards. These patents disclose inventions comprising a slit to lock a pair of wings of a winged needle assembly on each sidewall of the needle guards, slidably locking the wings after use according to locations and shapes of the slit, and retracting a needle in the needle guard.

However, these inventions are not satisfactory and have a room for further improvement about (1) easiness and stability to attach needle guards to winged needle assemblies, (2) operationality when inserting guarded winged needle assemblies to patients, and (3) operationality when shielding needles after use.

The inventors of the present invention proposed a new needle guard with a pair of protruded wings on both sides of a body (Patent Publication No. 2001-327599 (P2001-327599A)). A winged needle assembly after use is retracted in the above-mentioned needle guard, the wings are bended upward, and locked with stoppers in the wings. The winged needle assembly does not protrude from the needle guard.

But the presence of a tube connected to the support of the winged needle assembly makes it difficult for the needle guard to firmly retract and lock the needle inside the guard.

SUMMARY OF THE INVENTION

An object of this invention is to provide a needle guard which is attached to a winged needle assembly with a tube, and which enables to lock the needles safely and securely within the guard.

Another objects of this invention will be detailed hereinafter.

(Needle Guard)

(1) This invention provides an elongated cylindrical needle guard for attaching and protecting a medical needle to which a tube is connected, which comprises:
  a cylindrical body consisting of a front portion 2, a body 3 and a rear portion 4;
  an aperture 5 at the bottom of the body 3;
  at least two or more projecting portions 7a, 7b, 7c on the top wall of the cylindrical body from the front portion 2 to the rear portion 4;
  a slit 9 at the bottom of the rear portion 4 along a longitudinal direction of said needle guard; and
  a groove 22 for fixing the tube on the top of the rear portion 4; and
  projecting portions 23a, 23b facing to each other at the back of said groove 22.

(2) This invention provides a needle guard 1 according to the above (1), wherein
  a cutout portion 22a in said projecting portion 7c is formed in upwardly-widened tapered shape.

(Capped Needle Guard)

(3) This invention provides a capped needle guard 71, wherein
  a cap 18 is detachably attached to the front portion 2 of said needle guard 1 according to the above (1) or (2).

(4) This invention provides a capped needle guard 81, wherein
  a cap 28 is integrally molded via a rim 28a with the front portion 2 of said needle guard 1 according to the above (1).

(Guarded Winged Needle Assembly)

(5) This invention provides a guarded winged needle assembly 1A, 21A, 31A, wherein
  said needle guard 1 according to the above (1) or said capped needle guard 71, 81 according to the above (2) or (3) is attached to a winged needle assembly 10.

(6) This invention provides a guarded winged needle assembly 1A, comprising:
  a winged needle assembly 10, in which a needle pin 12 is attached to the front portion of a support 13, to which a pair of wings 14 is attached on both sides of the support, to which a needle cap 16 is attached on the front outside surface of the support, and to which a tube 15 is connected on the rear outside surface of the support; and
  a needle guard (1) according to the above (1) or (2) which is slidably mounted on said winged needle assembly 10; wherein
    in a situation that said winged needle assembly 10 is attached and retracted to said needle guard 1 through an aperture 5 and a slit 9,
    the outside surface of the needle cap 16 is attached to the inside surface of the front portion 2;
  said winged needle assembly 10 is fixed to said needle guard 1;
  the needle pin 12 is shielded in the needle cap 16;
  the needle pin 12 of said winged needle assembly 10 is exposed by uncapping the needle cap 16;

the needle pin 12 of said winged needle assembly 10 is retracted into said needle guard 1 by sliding said winged needle assembly toward the rear portion 4 of said needle guard 1; and the tube 15 is fixed into a groove 22 through projecting portions 23a, 23b facing to each other by backwardly pulling it and lifting it up; there by said winged needle assembly 10 being kept not to slide toward the front portion 2 of said needle guard 1 and the needle pin 12 of said winged needle assembly 10 being kept not to be exposed from said needle guard 1.

(7) This invention provides a guarded winged needle assembly 21A, 31A, comprising:

a winged needle assembly 10, in which a needle pin 12 is attached to a front portion of a support 13, to which a pair of wings 14 is attached to both sides of the support, and to which a tube 15 is connected to the rear outside surface of the support; and a capped needle guard 71,81 according to the above 3 or 4 which is slidably mounted on said winged needle assembly; wherein in a situation that said winged needle assembly 10 is attached and retracted to said capped needle guard 71, 81 through an aperture 5 and a slit 9;

the front outside surface of the support 13 is attached to the inside surface of the front portion 2 of said capped needle guard 71, 81;

said winged needle assembly 10 is fixed to said capped needle guard 71, 81;

the needle pin 12 is shielded in said capped needle guard 71, 81;

the needle pin 12 is exposed by uncapping said capped needle guard 71, 81;

the needle pin 12 of said winged needle assembly 10 is retracted into said capped needle guard 71,81 by sliding said winged needle assembly 10 toward the rear portion 4 of said capped needle guard 71, 81; and the tube 15 is fixed into a groove 22 through projecting portions 23a, 23b facing to each other by backwardly pulling it and lifting it up; there by said winged needle assembly 10 being kept not to slide toward the front portion 2 of said capped needle guard 71, 81 and the needle pin 12 being kept not to be exposed from said capped needle guard 71, 81.

(Needle Guard)

(8) This invention provides an elongated cylindrical needle guard 1 for attaching and protecting a medical needle to which a tube is connected, comprising:

a cylindrical body consisting of a front portion 2, a body 3 and a rear portion 4;

an aperture 5 at the bottom of the body 3;

a pair of stoppers 58 on both sides of the body 3;

thick portions 58b on each of the stoppers 58; and locking portions 58c on the back of each of the thick portions 58b for locking wings 14 of a winged needle assembly 10.

(9) This invention provides the needle guard 1 according to the above (8), further comprising a pair of second stoppers 68 on both sides of a rear portion 4.

(10) This invention provides a needle guard 1 according to the above (8) or (9), further comprising a groove 22 for fixing the tube on the top wall of the rear portion 4.

(11) This invention provides a needle guard 1 according to the above (10), further comprising:

a cutout portion 22'a at the back of the groove 22; and a narrow portion 22b between the groove 22 and the cutout portion 22'a.

(12) This invention provides a needle guard 1 according to any one of the above (8) to (11), further comprising:

projecting portions 7a, 7b on the top wall from the front portion 2 to the body 3;

a slit 9 at the bottom of the rear portion 4 along a longitudinal direction of said needle guard.

(Capped Needle Guard)

(13) This invention provides a capped needle guard 71, wherein a cap 18 is detachably attached at the front portion 2 of said needle guard 1 according to any on of the above (8) to (12).

(14) This invention provides a capped needle guard 81, wherein a cap 28 is integrally molded via a rim 28a with the front portion 2 of said needle guard 1 according to any one of the above (8) to (12).

(Guarded Winged Needle Assembly)

(15) This invention provides a guarded winged needle assembly 1A, 21A, 31A, where in said needle guard 1 according to any one of the above (8) to (12) or said capped needle guard 71, 81 according to the above (13) or (14) is mounted on the winged needle assembly 10.

(16) This invention provides a guarded winged needle assembly 1A, comprising:

a winged needle assembly 10, in which a needle pin 12 is attached to the front portion of a support 13, to which a pair of wings 14 is attached on both sides of the support, to which a needle cap 16 is attached the front outside surface of the support, and to which a tube 15 is connected on the rear outside surface of the support; and a needle guard 1 according to any one of the above (8) to (12) which is slidably mounted on said winged needle assembly 10; wherein in a situation that said winged needle assembly 10 is attached and retracted to said needle guard 1 through an aperture 5 and a slit 9, the outside surface of the needle cap 16 is attached to the inside surface of the front portion 2;

said winged needle assembly 10 is fixed to said needle guard 1;

the needle pin 12 is shielded in the needle cap 16;

the needle pin 12 of said winged needle assembly 10 is exposed by uncapping the needle cap 16;

the needle pin 12 of said winged needle assembly 10 is retracted into said needle guard 1 by sliding said winged needle assembly 10 toward the rear portion 4 of said needle guard 1; and locking portions 58c are locked to tips of the wings 14; there by said winged needle assembly 10 being kept not to slide toward the front portion 2 of said needle guard 1 and the needle pin 12 of said winged needle assembly 10 being kept not to be exposed from said needle guard 1.

(17) This invention provides a guarded winged needle assembly 21A, 31A, comprising:

a winged needle assembly 10, in which a needle pin 12 is attached to the front portion of a support 13, to which a pair of wings 14 is attached on both sides of the support, and to which a tube 15 is connected to the rear outside surface of the support; and a capped needle guard 71,81 according to the above (13) or (14) which is slidably mounted on said winged needle assembly 10; wherein in a situation that said winged needle assembly 10 is attached and retracted to said capped needle guard 71, 81 through an aperture 5 and a slit 9;

the front outside surface of the support 13 is attached to the inside surface of the front portion 2 of said capped needle guard 71, 81;

said winged needle assembly 10 is fixed to said capped needle guard 71, 81;

the needle pin 12 is shielded in said capped needle guard 71, 81;

the needle pin 12 is exposed by uncapping said capped needle guard 71, 81;

the needle pin 12 of said winged needle assembly 10 is retracted into said capped needle guard 71,81 by sliding said winged needle assembly 10 toward the rear portion 4 of said capped needle guard 71, 81; and locking portions 58c are locked to tips of the wings 14; there by said winged needle assembly 10 being kept not to slide toward the front portion 2 of said capped needle guard 71, 81 and the needle pin 12 of said winged needle assembly 10 being kept not to be exposed from said capped needle guard 71, 81.

(18) This invention provides a guarded winged needle assembly 1A, 21A, 31A according to the above (16) or (17), wherein the pair of wings 14 are crosswardly locked between the stoppers 58 and the second stoppers 68 by folding or bending the wings 14 upwards.

(19) This invention provides a guarded winged needle assembly 1A, 21A, 31A according to any one of the above (16) to (18), wherein the tube 15 are fixed in the groove 22 from the cutout portion 22a to the narrow portion 22b by backwardly pulling the tube and lifting it up.

(Protection Guard)

(20) This invention provides a protection guard 91 for the needle guard 1 according to the above (1) or (8), comprising a front attachment portion 91f and a rear portion attachment portion 91b on both sides of plate 91a, respectively, wherein said front attachment portion 91f and said rear portion attachment portion 91b are attached to the front portion 2 and the rear portion 4 of said needle guard 1, respectively; there by the aperture 5 at the body 3 of said needle guard 1 being covered to cover the needle and the support of said winged needle assembly.

(21) This invention provides a protection guard 92 for a needle guard 1 according to the above (1) or (8), comprising a front attachment portion 92f on a plate 92a; and said front attachment portion 92f is attached to the front portion 2 of said needle guard 1, wherein a portion of the aperture 5 at the body 3 of said needle guard 1 is covered by the plate 92a so that at least the needle is not exposed.

BRIEF DESCRIPTION OF THE DRAWINGS

FIG. 1 is a schematic view of a preferred embodiment of the needle guard of the present invention; FIG. 1c is a perspective view of the FIG. 1a apparatus, in a plane rotated by 180° with respect to the plane of FIG. 1a.

FIG. 3 is a perspective view showing usage of the guarded winged needle assembly 1A; FIGS. 3a to 3f are views showing the same as time series; and FIG. 3f1 is an enlarged view of the vicinity of the projecting portion 7c shown in FIG. 3f;

FIG. 4 is a schematic view of a preferred embodiment of the capped needle guard of the present invention; FIG. 4a is a front perspective view of this capped needle guard 71; FIG. 4b is a rear perspective view of the same; FIG. 4c is a perspective view of the FIG. 4a apparatus; in a plane rotated by 180° with respect to the plane of FIG. 4a; and FIG. 4d is a perspective view of the FIG. 4b apparatus, in a plane rotated by 180° with respect to the plane of FIG. 4b;

FIG. 6 is a perspective view showing usage of the guarded winged needle assembly 21A; FIGS. 6a to 6f are views showing it as time series; and FIG. 6f1 is an enlarged view at the vicinity of the projecting portion 7c shown in FIG. 6f;

FIG. 7 is a schematic view of a preferred embodiment of the capped needle guard of the present invention; FIG. 7a is a front perspective view of this inventive capped needle guard 81; FIG. 7b is a rear perspective view of the same; FIG. 7c is a perspective view of the FIG. 7a apparatus, in a plane rotated by 180° with respect to the plane of FIG. 7a; and FIG. 7d is a perspective view of the FIG. 7b apparatus, in a plane rotated by 180° with respect to the plane of FIG. 7b;

FIG. 9 is a perspective view showing usage of the guarded winged needle assembly 31A; FIG. 9a to FIG. 9f are views showing as time series, and FIG. 9f1 is an enlarged view at the vicinity of the projecting portion 7c in FIG. 9f;

FIG. 10 is a schematic view of a preferred embodiment of the needle guard of the present invention; FIG. 10c is a perspective view of the FIG. 10a apparatus, in a plane rotated by 180° with respect to the plane of FIG. 10a.

FIG. 11 is a developed view of a preferred embodiment of the needle guard 1 of the present invention.

FIG. 14 is a developed view of the FIG. 12d apparatus with the needle guard 1 attached to the winged needle assembly 10.

FIG. 16 is a schematic view of a preferred embodiment of the capped needle guard of the present invention; FIG. 16a is a front perspective view of the capped needle guard 71; FIG. 16b is a rear perspective view of it; FIG. 16c is a perspective view of the FIG. 16a apparatus, in a plane rotated by 180° with respect to the plane of FIG. 16a; and FIG. 16d is a perspective view of the FIG. 16b apparatus, in a plane rotated by 180° with respect to the plane of FIG. 16b;

FIG. 19 is a schematic view of a preferred embodiment of the capped needle guard of the present invention; FIG. 19a is a front perspective view of the capped needle guard 81; FIG. 19b is a rear perspective view of the same; FIG. 19c is a perspective view of the FIG. 19a apparatus, in a plane rotated by 180° with respect to the plane of FIG. 19a, and FIG. 19d is a perspective view of the FIG. 19b apparatus, in a plane rotated by 180° with respect to the plane of FIG. 19b;

FIG. 22 is a view showing how to attach a protection guard to this needle guard of the present invention.

DESCRIPTION OF THE PREFERRED EMBODIMENT

In order to accommodate and lock a winged needle assembly more safely and securely in a needle guard, this needle guard is classified as a needle guard with a locking groove and a needle guard with locking stoppers. The former will be detailed hereinafter and the later will be described after that.

(Needle Guard with a Locking Groove, Needle Cap, Winged Needle Assembly)

Here is described an embodiment of a needle guard with a locking groove, a needle cap used with this needle guard, and a winged needle, to which they are attached, for protection with reference to their drawings.

FIGS. 1 to 3 are the examples of the needle guard, the needle cap, and the winged needle assembly.

FIG. 1 is a schematic view of a preferred embodiment of the needle guard of the present invention. FIG. 1a is a front perspective view of this needle guard 1. FIG. 1b is a rear perspective view of the same. FIG. 1c is a perspective view of the FIG. 1a apparatus, in a plane rotated by 180° with respect to the plane of FIG. 1a, and FIG. 1d is a perspective view of the FIG. 1b apparatus, in a plane rotated by 180° with respect to the plane of FIG. 1b.

Figure 1A:
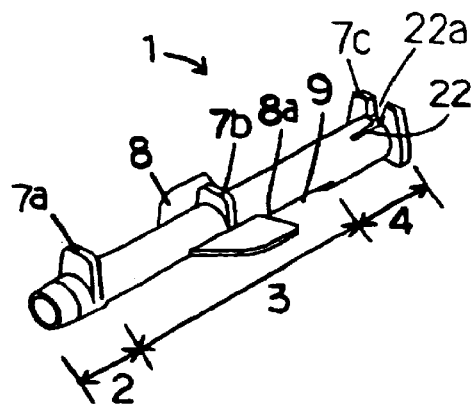
FIG. 1a is a front perspective view of this needle guard 1.
Figure 1B:
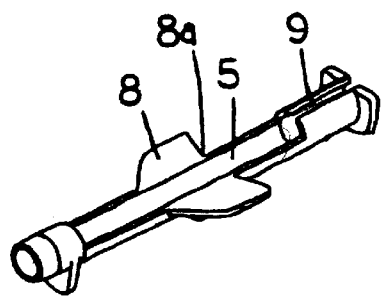
FIG. 1b is a rear perspective view of the same.
Figure 1C:
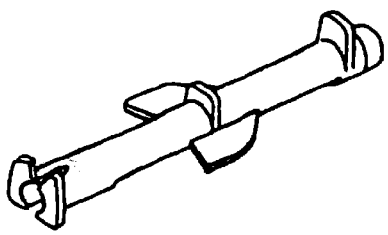
Figure 1D:
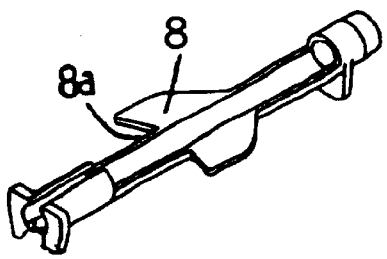
FIG. 1d is a perspective view of the FIG. 1b apparatus, in a plane rotated by 180° with respect to the plane of FIG. 1b.

As shown in FIGS. 1a to 1d, this needle guard 1 is an elongated cylinder(cylindrical body) from the front to the rear. As shown in FIG. 1a, this cylindrical body is separated into approximate three parts by the front portion 2, the body 3, and the rear portion 4. In this case, an aperture 5 is formed at the bottom of the body 3 as shown in FIG. 1b. Also shown in FIG. 1a and others, two or more projecting portions, e.g., projecting portions 7a, 7b, and 7c are respectively formed on the top wall of the front portion 2, the body 3, and the rear portion 4. A pair of projecting stoppers 8 may be formed on both sides of the body 3.

Areas of the front portion 2, the body 3, and the rear portion 4 shown in the drawings of this invention are tentative. The area with the projecting portion 7a defines the front portion 2. The area with the projecting portion 7b, the aperture 5, and the projecting stoppers 8 defines the body 3, and the area with the projecting portion 7c and a slit 9 which will be described later defines the rear portion 4. Therefore, the areas of the front portion 2, the body 3, and the rear portion 4 are varied according to the location of the projecting portions 7a, 7b, 7c, and the slit 9, and the length of the aperture 5.

As described later, the projecting portions 7a, 7b, and 7c are the parts medical workers grasp with their fingers when using this guarded winged needle assembly of the present invention. They, as gripping ribs, should be substantially square and plate-shaped, as shown in FIG. 1. Especially in the cases of 7a and 7c, the width along the cross section of the needle guard 1 should be substantially the same with or bigger than that of the needle guard 1 so that the medical workers can easily grasp them with their fingers.

The shape, the location, and the number of the projecting portions 7a, 7b, and 7c of this invention are not limited to the ones described in the drawings. Their designs can be modified/changed as long as the medical workers can easily grasp the needle guard 1.

At the bottom of the rear portion 4 of the needle guard, as shown in FIG. 1b, the slit 9 is formed along the longitudinal direction of the needle guard so that a tube 15 of a winged needle assembly 10 can be inserted therein.

As shown in FIG. 1a, from the top of the rear portion 4 of the needle guard 1 to the projecting portion 7c, a groove 22 to fix the tube (groove for fixing) is formed. A cutout portion 22a is formed in upwardly-widened tapered shape.

The groove 22, as shown in FIG. 3f1 that will be described later, should be preferably formed wide enough to fix at least the tube 15, and this groove 22 should be preferably formed in tapered shape becoming wider toward the entrance. The thus tapered cutout portion 22a and/or the groove 22 can surely fix the tube 15 in the groove 22.

As shown in FIG. 3f1, projecting portions 23a and 23b are formed facing with each other at the back of the groove 22. The shape of these projecting portions 23a and 23b can be anything, e.g., a triangle, a square, a semicircle, or whisker-shaped so that the tube 15 fixed in the groove 22 is unable to slip backwardly from there.

The projecting portions 23a and 23b should be preferably made with such elastic materials that they would not be broken or bent when at least the tube 15 passes between them.

The projecting portions 23a and 23b should be preferably narrow and made with materials that vibrate or make a pop sound so that medical workers can recognize the movement of the portion 23a and 23b when the tube 15 passes between them.

(Attachment of a Needle Guard to a Winged Needle Assembly)

Here is a description of how to set up a guarded winged needle assembly 1A by attaching a needle guard 1 to a winged needle assembly 10.

As shown in FIG. 2, the winged needle assembly 10 of the present invention is formed by inserting a needle pin 12 at the front of a needle support (or hub) 13, attaching a pair of wings 14 on both sides of the support 13, and connecting the tube 15 on the rear outside surface. A cylindrical or tapered needle cap 16 is attached to the front outside surface of the support for protecting the needle before use or during in storage.

The needle pin 12 and the support 13 of the winged needle assembly 10 are slidably mounted on or accommodated into the cylindrical needle guard 1 through an aperture 5 shown in FIG. 1b from the bottom of the needle guard 1 in the direction shown in FIG. 1a. The tube 15 connected to the support is mounted on the rear portion 4 through a slit 9. Here "slidably mounted" means the winged needle assembly and the needle guard can slide relatively with each other. This means the winged needle assembly 10 can slide backwards on the basis of the needle guard 1. Also, the needle guard 1 can slide forwards on the basis of the winged needle assembly 10.

Figure 2A:
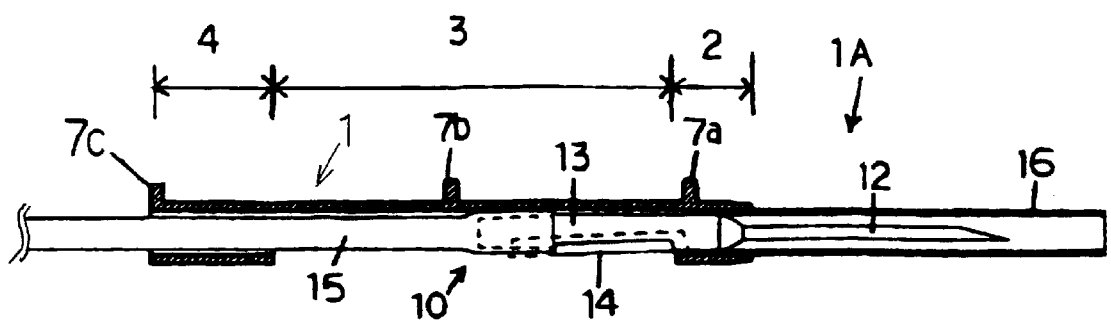
FIG. 2 is a cross-sectional view of the guarded winged needle assembly 1A with the needle guard 1 shown in FIG. 1 attached to the winged needle assembly 10.
Figure 2B:

In this case, as shown in FIG. 2a, the needle cap 16 attached to the front outside surface of the support fits the inside surface of the front portion 2 of the guard and engaged. The winged needle assembly 10 is attached and fixed to the needle guard 1, and the needle pin 12 is kept shielded by the needle cap 16. This is how the guarded winged needle assembly 1A is formed.

(Usage of a Winged Needle Assembly)

FIG. 3 is a perspective view showing usage of a guarded winged needle assembly 1A by showing it as time series from FIGS. 3a to 3f. FIG. 3f1 is an enlarged view of a circled part of FIG. 3f (at the vicinity of the projecting portion 7c). FIG. 2a corresponds to FIG. 3a, FIG. 2b to FIG. 3e, and FIG. 2d to FIG. 3f, respectively.

Here is a description of usage of the guarded needle winged assembly 1A with reference to FIGS. 3a to 3f.

① As shown in FIG. 3a, the guarded needle winged assembly 1A, or projecting portions 7a, 7b, and 7c of the needle guard 1 are turned upwards.

② As shown in FIG. 3b, both sides of the projecting portion 7c are picked up with the e.g., left (right) thumb and the forefinger. A pair of wings 14 are also picked up with the right (left) thumb and the forefinger so that they are folded upwards.

③ As shown in FIG. 3c, a needle cap 16 is taken off so that a needle pin 12 is exposed from the needle guard 1.

④ The needle pin 12 of the guarded winged needle assembly 10 is inserted into a patient's e.g. arm with a pair of wings 14 folded upwards with the right (left) thumb and the forefinger, as shown in FIG. 3d.

⑤ Following insertion of the needle into the patient, the wings 14 are unfolded and taped to the patient's skin with an adhesive tape so the inserted needle does not move from an inserted portion of the patient's skin, as shown in FIG. 3e. Dialysis, blood and/or fluid infusion start at this stage.

⑥ After dialysis or else is finished, as shown in FIG. 3f, the needle pin 12 of the guarded winged needle assembly 1A is extracted from the inserted portion, and the winged needle assembly 10 is slid into the needle guard by pulling the tube 15 backwards.

Figure 2C:
Figure 2D:
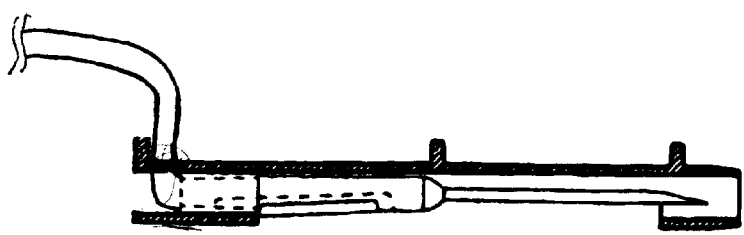

To be more precise, while the adhesive tape is taken off and the inserted portion of the patient's skin is sterilized by sterilized cotton with his or her left (right) ring finger, his or her middle finger and forefinger are used to hold the projecting portions between 7a and 7b, or between 7b and 7c. Then, for example, as shown in FIG. 2c, the tube 15 at the vicinity of the rear portion 4 of the needle guard is pulled backwards with his or her right (left) hand, and a winged needle assembly 10 is slid and retracted into the needle guard 1. As shown in FIG. 2d and especially FIG. 3f1, the tube 15 is pulled upwards, lifted up, and fixed to a groove 22 by passing through projecting portions 23a and 23b.

According to this invention, the tube 15 of the winged needle assembly 10 which used to be free and unfixed will be fixed into the groove 22 located from the top wall of the rear portion 4 of the needle guard to the projecting portion 7c with the help of projecting portions 23a and 23b. This invention makes it possible to avoid accidental exposure of the needle pin 12.

(Attachment of a Capped Needle Guard to a Winged Needle Assembly)

According to this invention, a capped needle guard can be used as a substitute of a needle cap when used with a needle guard. Here is a description of a capped needle guard and its attachment to a winged needle assembly. FIGS. 4 to 6 are the drawings of this description.

FIG. 4 is a schematic view of a preferred embodiment of this capped needle guard of the invention; FIG. 4a is a front perspective view of this capped needle guard 71; FIG. 4b is a rear perspective view of the same; FIG. 4c is a perspective view of the FIG. 4a apparatus; in a plane rotated by 180° with respect to the plane of FIG. 4a, and FIG. 4d is a perspective view of the FIG. 4b apparatus, in a plane rotated by 180° with respect to the plane of FIG. 4b.

As shown in FIG. 4, the capped needle guard 71 of the invention has a detachably-attached cap 18 on the front end portion 2 of the cylindrical needle guard 1. The only difference between the capped needle guard 71 shown in FIG. 4 and the needle guard 1 shown in FIG. 1 is whether or not the guard has an pre-attached cap. Other features such as an aperture 5 at the bottom of the body 3 of this capped needle guard, projecting portions 7a, 7b, and 7c on the top wall of the front portion 2, the body 3, and the rear portion 4, a slit 9 to insert a tube 15 of a winged needle assembly 10 at the bottom of the rear portion 4 along the longitudinal direction of the needle guard, and a groove 22 for fixing the tube from the top wall of the rear portion 4 to the projecting portion 7c, and projecting portions, 23a and 23b facing to each other on the rear part of the groove 22, are all the same. Therefore, detailed description will be omitted.

A guided winged needle assembly 21A can be set up in the same way as the needle guard 1 by attaching a capped needle guard 71 to the winged needle assembly 10.

Figure 5A:
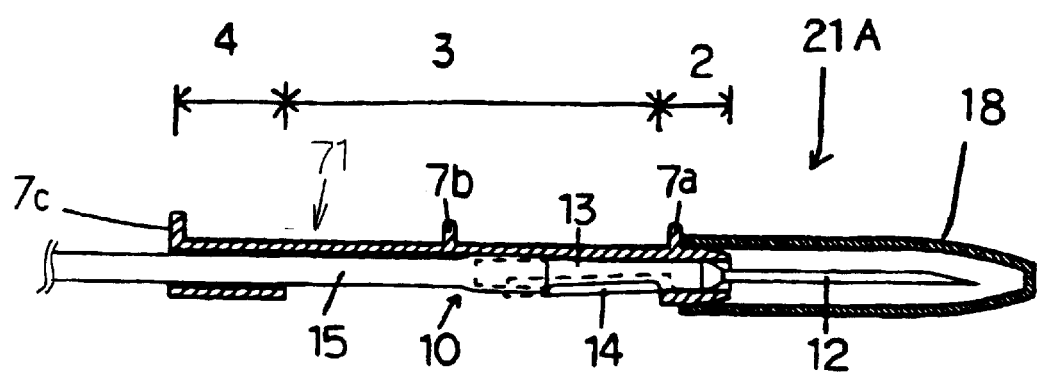
FIG. 5 is a cross-sectional view of the guarded winged needle assembly 21A with the capped needle guard 71 shown in FIG. 4 attached to the winged needle assembly 10.
Figure 5B:
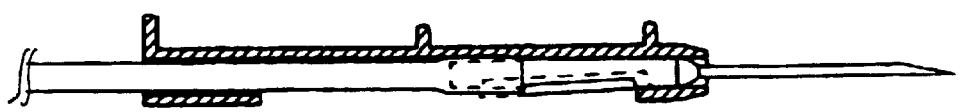
Figure 5C:
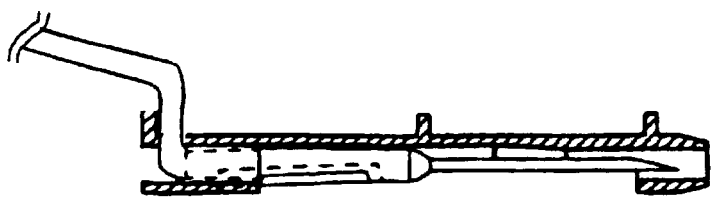

FIG. 5 is a cross-sectional view of the guarded winged needle assembly 21A with the capped needle guard 71 shown in the FIG. 4 apparatus attached to a winged needle assembly 10. As shown in FIG. 5a, the winged needle assembly 10 and the capped needle guard 71 are fixed and engaged by attaching the front outside surface of the support 13 to the inside surface of the front portion 2 of the capped needle guard 71. The needle pin 12 is kept shielded by the capped needle guard 71 (especially by the cap 18).

FIG. 6 is a perspective view showing usage of a guarded winged needle assembly 21A by drawing it as time series from FIGS. 6a to 6f. FIG. 6f1 is an enlarged view of a circled part of FIG. 6 (at the vicinity of the projecting portion 7c). FIG. 5a corresponds to FIG. 6a, FIG. 5b to FIG. 6e, and FIG. 5c to FIG. 6f, respectively.

As shown in FIGS. 6a to FIG. 6f, the guarded winged needle assembly 21A is used by the above-mentioned ① through ⑥ procedures basically in the same way as the guarded winged needle assembly 1A. The only difference between the guarded winged needle assembly 21A and its counterpart 1A is that with the former the detachably-attached cap 18 on the front portion 2 of the needle guard is taken off to expose the needle pin 12 of the winged needle assembly 10 from the capped needle guard 71.

(Alternative Embodiment of a Capped Needle Guard)

FIG. 7 to FIG. 9 show an alternative embodiment of a capped needle guard.

FIG. 7 is a schematic view of an alternative embodiment of the capped needle guard of the present invention; FIG. 7a is an front perspective view of this capped needle guard 81; FIG. 7b is a rear perspective view of it; FIG. 7c is a perspective view of the FIG. 7a apparatus, in a plane rotated by 180° with respect to the plane of FIG. 7a, and FIG. 7d is a perspective view of the FIG. 7b apparatus, in a plane rotated by 180° with respect to the plane of FIG. 7b.

As shown in FIG. 7, the capped needle guard 81 of the present invention is formed by attaching a cap 28 integrally molded via a rim (break-away part) 28a with the front portion 2 of the needle guard 1. A pair of ribs for manually gripping (not shown in drawings) can be at least symmetrically formed on the outside surface of the cap 28 so that the integrally molded cap 28 can be easily uncapped. The only difference between the capped needle guard 81 shown in FIG. 7 and the capped needle guard 71 shown in FIG. 4 is whether the cap is integrally molded with or detachably attached to the front portion of the needle guard. Detailed descriptions will be omitted because all other features are the same.

A guided winged needle assembly 31A can be set up in the same way as the needle guard 71 by attaching the capped needle guard 81 to the winged needle assembly 10.

Figure 8A:
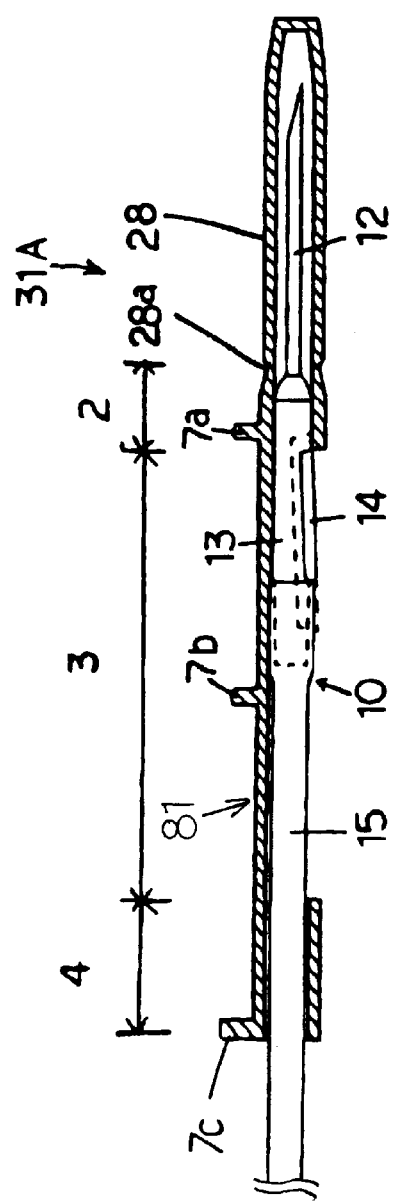
FIG. 8 is a cross-sectional view of an alternative embodiment of the guarded winged needle assembly 31A with the capped needle guard 81 attached to a winged needle assembly 10.
Figure 8B:
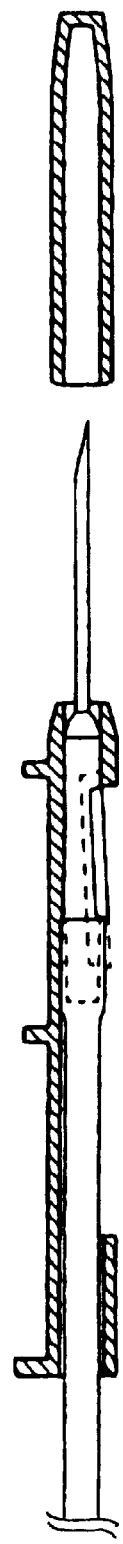
Figure 10A:
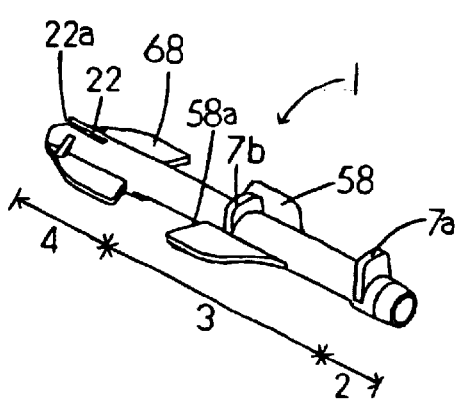
FIG. 10a is a front perspective view of the needle guard 1.
Figure 10B:
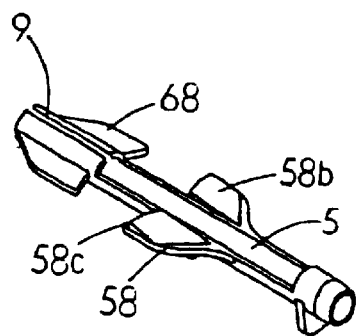
FIG. 10b is a rear perspective view of it.
Figure 10C:
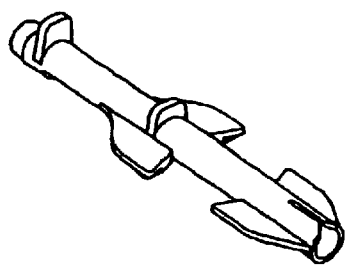
Figure 10D:
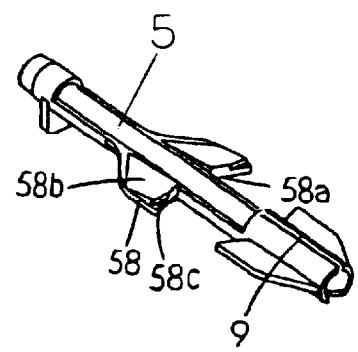
FIG. 10d is a perspective view of the FIG. 10b apparatus, in a plane rotated by 180° with respect to the plane of FIG. 10b.

FIG. 8 is a cross-sectional view of a guarded winged needle assembly 31A with a capped needle guard 81 shown in FIG. 7 apparatus attached to a winged needle assembly 10. As shown in FIG. 8a, the winged needle assembly 10 and the capped needle guard 81 are fixed by attaching the front outside surface of a support 13 to the inside surface of the front portion 2 of the capped needle guard 81. The needle pin 12 is kept shielded by the capped needle guard 81 (especially by the cap 28).

FIG. 9 is a perspective view showing usage of a guarded winged needle assembly 31A by showing it as time series from FIGS. 9a to 9f. FIG. 9f1 is an enlarged view of a circled part of FIG. 9f (at the vicinity of the projecting portion 7c). FIG. 8a corresponds to FIG. 9a, and FIG. 8b to FIG. 9e, respectively.

As shown in FIG. 9a to FIG. 9f, the guarded winged needle assembly 31A is used by the above-mentioned ① through ⑥ procedures basically in the same way as the guarded winged needle assemblies 1A and 21A. The only difference the guarded winged needle assembly 31A has compared to its counterparts 1A and 21A is that with the former the cap 28 is taken off from the rim 28a (break-away portion) and expose the needle pin 12 of the winged needle assembly 10 from the capped needle guard 81.

(Needle Guard with Stoppers, Needle Cap, Winged Needle Assembly)

Here is a description of the needle guard with stoppers of the present invention and others with reference to the drawings.

FIGS. 10 to 15 are the needle guard with stoppers of the present invention, the needle cap used with this needle guard with stoppers, and the winged needle assembly to which these needle guard and needlecap are attached or mounted for protection. This winged needle assembly itself is identical to the one described before. A pair of wings 14 is attached to the both sides of the support.

FIG. 10 is a schematic view of a preferred embodiment of the needle guard of the present invention; FIG. 10a is an front perspective view of the needle guard 1; FIG. 10b is a rear perspective view of the same; FIG. 10c is a perspective view of the FIG. 10a apparatus, in a plane rotated by 180° with respect to the plane of FIG. 10a, and FIG. 10d is a perspective view of the FIG. 10b apparatus, in a plane rotated by 180° with respect to the plane of FIG. 10b.

FIG. 11 is a developed view of this needle guard 1 of the present invention; FIG. 11a is a plan view of the same; FIG. 11b is a side view of the same; FIG. 11c is a plan view of backside of FIG. 11a apparatus; and FIG. 11d is an enlarged view at the vicinity of a groove 22.

This needle guard 1 of the present invention is, as shown in FIG. 10, is cylindrical. An aperture 5 is formed at the bottom of the body 3, and a pair of stoppers 58, which outwardly project, are formed on both sidewalls of the body 3. Thick portions 58b are formed at the back of the stoppers 58 so that they become gradually thicker toward the back portion. Step-shaped locking portions 58c are formed at the back of the thick portions 58b (see FIGS. 11b and 11c). The locking portions 58c are formed to lock the tips of the wing 14 of the winged needle assembly retracted into the needle guard. The second pair of stoppers 68 are preferably formed on both sidewalls of the rear portion 4.

As shown in FIG. 10, the stoppers 58 and 68 are formed as outwardly-projecting wing-shaped on both sides of the body 3 and the rear portion 4. The shape of the stoppers is not limited to "wing-shaped" as long as the stoppers are blade-shaped and deform or bent upward or downward but are not broken or cracked by force from above or below and capable of locking the wings. It can be a substantial square or semicircle. Stoppers are thus preferably made with semi-rigid or rigid materials so they are able to deform upward or downward when locking the wings.

Figure 11A:
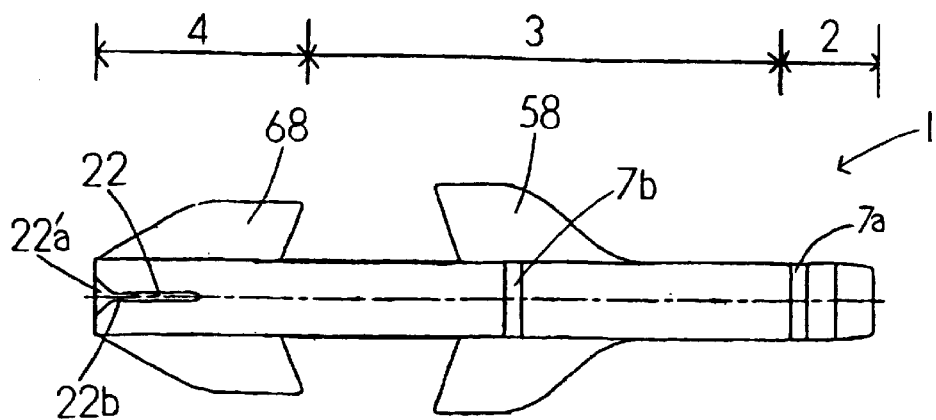
FIG. 11a is a plan view of the same.
Figure 11B:
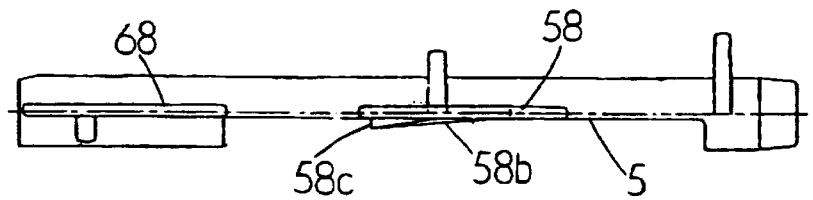
FIG. 11b is a side view of the same.
Figure 11C:
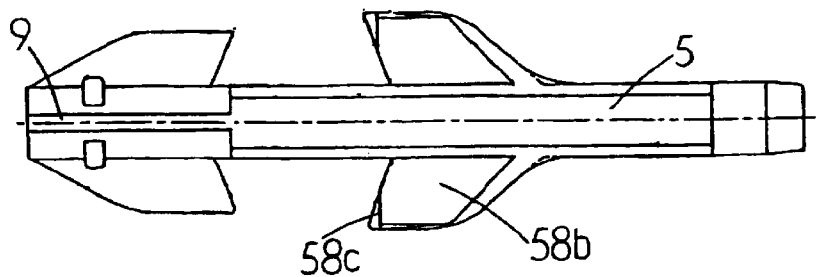
FIG. 11c is a backside plan view of the FIG. 11a apparatus.
Figure 11D:
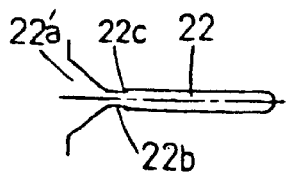
FIG. 11d is an enlarged view of a groove 22.

As shown in FIGS. 11a and 11d, from the substantial middle part to the back end on the top wall of the rear portion 4 of the needle guard 1, a groove 22 and a cutout portion 22'a are formed, and a narrow portion 22b is formed between the groove 22 and the cutout portion 22'a. The cutout portion 22'a is formed on the rear portion 4 in a tapered shape widening toward the rear end.

The groove 22 is formed to pinch and fix the tube 15 connected to the winged needle assembly. The narrow portion 22b is narrower than the groove 22, and the tube 15 inserted from the tapered cutout portion 22'a is pinched and fixed to the groove 22 through the narrow portion 22b.

Therefore, the groove 22 is formed wide enough to pinch and fix at least the tube 15. A horn portion 22c is formed in the narrow portion 22b so that the tube 15 pinched and fixed in the groove 22 will not come off toward the cutout portion 22'a.

The projecting portions 7a and 7b are preferably formed for manual gripping so that the needle guard 1 does not move when holding the top walls of the front portion 2 and the body 3 of the needle guard 1 with fingers during use.

At the bottom of the rear portion 4, as shown in FIG. 11c, the slit 9 is formed so that a tube 15 of the winged needle assembly 10 can be inserted along the longitudinal direction of the needle guard 1. The tube 15 can be inserted through an aperture 5 to the rear portion 4 of the cylinder without the slit 9, which will be described later.

(Attachment of a Needle Guard to a Winged Needle Assembly)

FIG. 12 is a cross-sectional view of a guarded winged needle assembly 1A with a needle guard 1 with stoppers shown in FIG. 10 apparatus attached to a winged needle assembly 10. As shown in FIG. 12, the way of setting up the guarded winged needle assembly 1A by attaching a needle guard 1 to the winged needle assembly 10 is basically the same as the way described in FIG. 2. Therefore, only the differences will be detailed hereinafter.

Figure 12A:
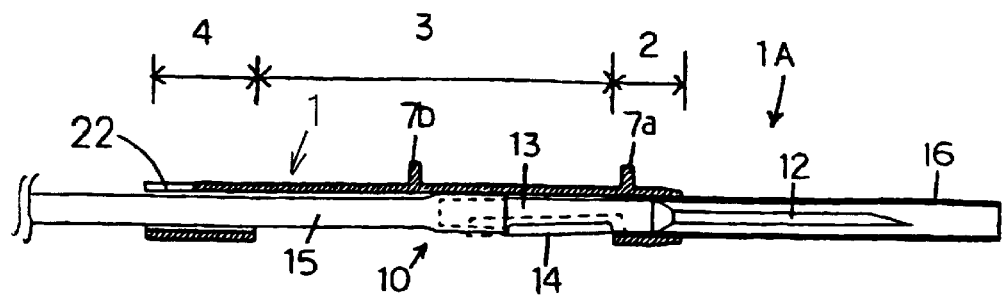
FIG. 12 is a cross-sectional view of the guarded winged needle assembly 1A with the needle guard 1 shown in the FIG. 10 apparatus attached to the winged needle assembly 10.
Figure 12B:

As shown in FIG. 12a, before use or when stored, the winged needle assembly 10 is installed or accommodated inside the needle guard 1 through an aperture 5 and a slit 9. The outside surface of the bottom of the needle cap 16 is fixed by attaching the inside surface of the front portion 2. Furthermore, the needle pin 12 is kept shielded by the needle cap 16, and taking off the needle cap 16 exposes the needle pin 12 of the winged needle assembly 10 during use, as shown in FIG. 12b.

Figure 12C:
Figure 12D:
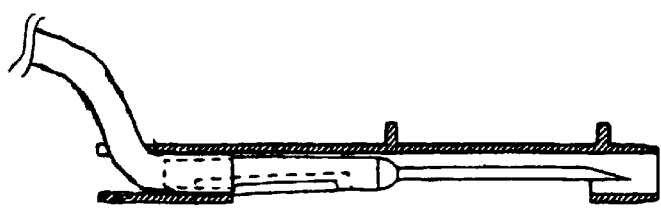

As shown in FIG. 12c, after use, the winged needle assembly 10 is slid back toward the rear portion 4 of the needle guard 1 and the needle pin 12 of the assembly 10 is retracted into the winged needle assembly 1 and simultaneously locking portions 58c lock the tips of the pair of wings 14. Furthermore, as shown in FIG. 12d, the tube 15 is pinched and fixed to the groove 22 through the narrow portion 22b from the cutout portion 22'a by pulling the tube 15 backwards and lifting it up.

This is how the needle pin 12 of the winged needle assembly 10 is not slid toward the front portion 2 and exposed out of the needle guard 1.

Figure 13D:
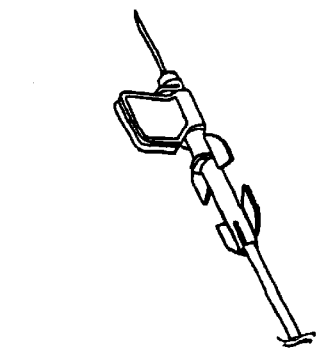
FIG. 13 is a perspective view showing usage of the guarded winged needle assembly 1A by showing it as time series from FIGS. 13a to 13h.
Figure 13C:
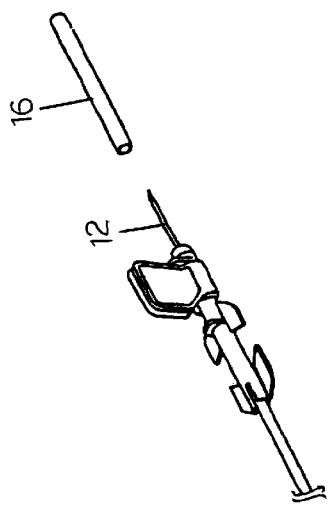
Figure 13B:
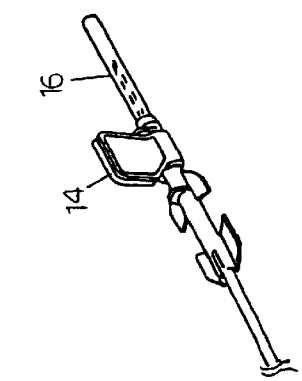
Figure 13A:
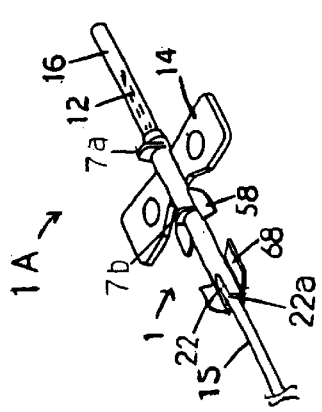
Figure 13H:
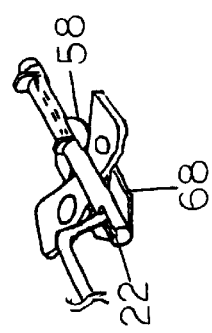
Figure 15A:
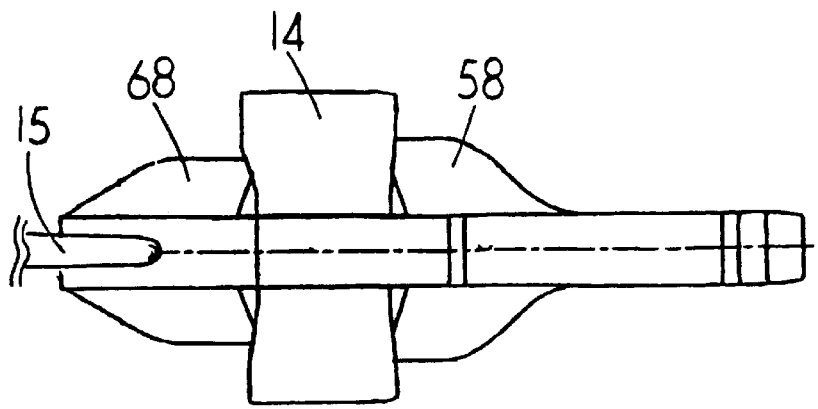
FIG. 15 is a generally substantial developed view of FIG. 14 apparatus with the needle guard 1 attached to the winged needle assembly 10.
Figure 15B:
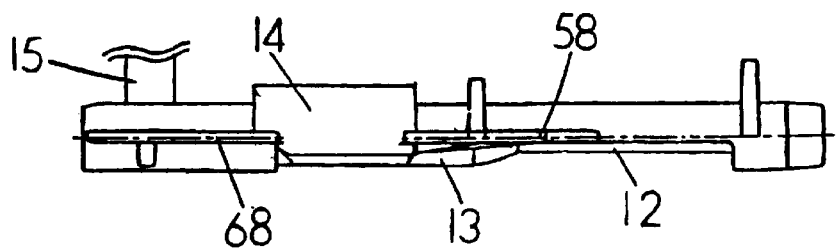
Figure 15C:
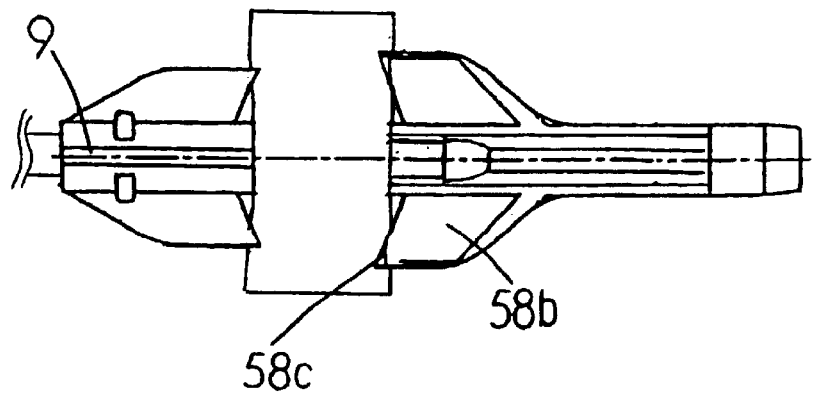

As shown in FIGS. 13h and 15, the pair of wings 14 are crossed and locked between the stoppers 58 and 68 by bending the wings upwards, and the needle pin 12 of the winged needle assembly 10 is kept firmly not to slide toward the front portion 2 and exposed from the needle guard 1.

(Usage of a Guarded Winged Needle Assembly)

Figure 13G:
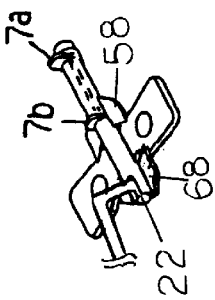
Figure 13F:
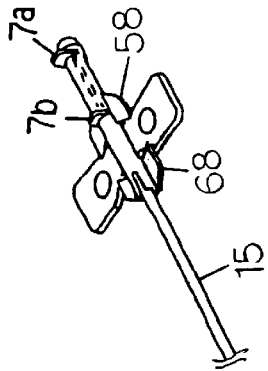

FIG. 13 is a perspective view showing usage of a guarded winged needle assembly 1A; by showing it as time series of FIGS. 13a to 13h. FIG. 14 is a developed view of the FIG. 13f apparatus; FIG. 14a is a plan view of the same; FIG. 14b is a side view of the same; FIG. 14c is a backside plan view of the FIG. 14a apparatus. FIG. 15 is a developed view of the FIG. 13h apparatus. Here is a description of usage of a guarded winged needle assembly 1A with reference to FIGS. 13a through 13h.

① As shown in FIG. 13a, projecting portions 7a, and 7b of the needle guard 1 of the guarded winged needle assembly 1A are turned upwards ② As shown in FIG. 13b, a pair of wings 14 is picked up with the right (left) thumb and the forefinger so that they are folded upwards.

③ As shown in FIG. 13c, a needle cap 16 is taken off so that a needle pin 12 is exposed from a needle guard 1 of the guarded winged needle assembly 10.

④ The needle pin 12 is inserted into a patient's e.g. arm with a pair of wings 14 folded upwards with the right (left) thumb and the forefinger, as shown in FIG. 13d.

Figure 13E:
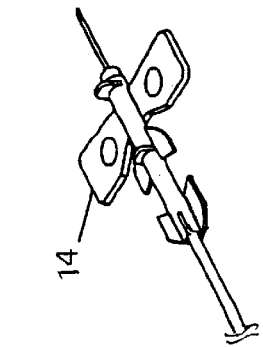
Figure 14A:
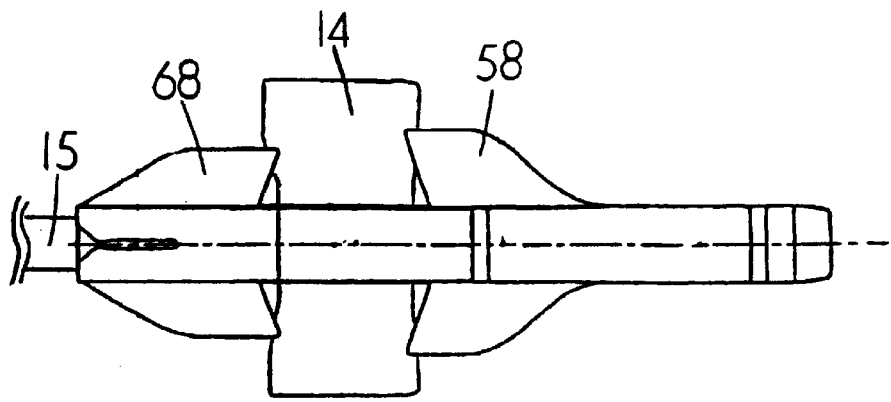
FIG. 14a is a plan view of the same.
Figure 14B:
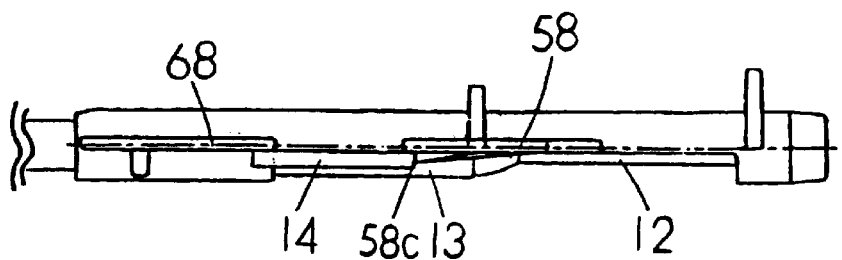
FIG. 14b is a side view of the same.
Figure 14C:
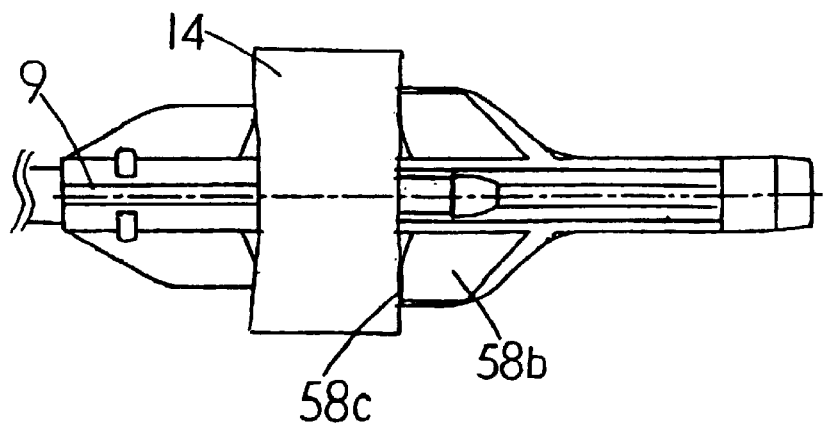
FIG. 14c is a backside plan view of the FIG. 14a apparatus.

⑤ Following insertion of the needle into the patient, the wings 14 are unfolded and taped to the patient's skin with an adhesive tape so the inserted needle does not move from the inserted portion of the patient's skin, as shown in FIG. 13e. Dialysis, blood and/or fluid infusion start at this stage, which was described before.

⑥ After dialysis or else is done, as shown in FIG. 13f, the needle pin 12 of the guarded winged needle assembly 1A is extracted from the inserted portion, and a winged needle assembly 10 is slid and retracted into the needle guard by pulling the tube 15 backwards. These procedures were described before.

To be more precise, the adhesive tape is taken off, and the inserted portion of the patient's skin is sterilized by sterilized cotton with his or her left (right) ring finger. His or her middle finger and forefinger are used to hold the projecting portions between 7a and 7b, or the back of 7b. Then, for example, as shown in FIG. 13f, the tube 15 at the vicinity of the rear portion 4 is pulled backwards with his or her right (left) hand, and a winged needle assembly 10 is slid and retracted into the needle guard 1.

As shown in FIG. 14, the tips of the pair of wings 14 are firmly fixed and locked with the locking portions 58c on the top of stoppers 58, and therefore, the needle pin 12 is assuredly not to protrude or extract from the needle guard 1.

⑦ As shown in FIG. 13g, the tube 15 is pulled upwards, lifted up, and pinched by and fixed in the groove 22 passing through a narrow portion 22b from a cutout portion 22'a (see FIGS. 11a and 11d). This pinching/fixing of the tube 15 in the groove 22 prevents the needle pin 12 from protruding from the front end of the needle guard.

The above-mentioned situation, where the tube 5 is pinched by the groove 22, blocks flow-line in the tube 15, thereby preventing blood remaining in the tube 15 from dripping out the tip of the needle pin 12. Thus, blood which remains inside the needle guard assembly 10 does not spatter.

⑧ To be safer, as shown in FIGS. 13h and 15, the pair of the wings 14 can be folded upwards, and therefore, the tips and parts of rear portion of the wing 14 are crossed and locked with the rear portion of the first stopper 58 and the tips of the second stopper 68, thereby the wings and stoppers are fixed together more strongly and tightly. The winged needle assembly 10 is not slid out of the front portion 2 of the needle guard 1, and is firmly locked inside the needle guard 1 without being exposed.

(Attachment of a Capped Needle Guard to a Winged Needle Assembly)

As described in the needle guard with locking grooves section, a capped needle guard with stoppers can be used as a substitute of a needle cap in combination with a needle guard. Here is a description of a capped needle guard and its attachment to a winged needle assembly.

FIGS. 16 to 18 are the drawings of the capped needle guard with stoppers and its attachment to the winged needle assembly.

FIG. 16 is a schematic view of a preferred embodiment of the capped needle guard of the present invention; FIG. 16a is an front perspective view of the capped needle guard 71; FIG. 16b is a rear perspective view of the same; FIG. 16c is a perspective view of the FIG. 16a apparatus, in a plane rotated by 180° with respect to the plane of FIG. 16a, and FIG. 16d is a perspective view of the FIG. 16b apparatus, in a plane rotated by 180° with respect to the plane of FIG. 16b.

As described before, the capped needle guard 71 of the present invention has a cap 18 detachably attached on the front portion 2 of the needle guard 1 in advance, as shown in FIG. 16.

A guided winged needle assembly 21A can be set up in the same way as the needle guard 1 by attaching the capped needle guard 71 to the winged needle assembly 10.

FIG. 17 is a cross-sectional view of the guarded winged needle assembly 21A with a capped needle guard 71 shown in FIG. 16 apparatus attached to a winged needle assembly 10. As shown in FIG. 17a, the winged needle assembly 10 and the capped needle guard 71 are fixed by attaching the front outside surface of the support 13 to the inside surface of the front portion 2 of the capped needle guard 71. The needle pin 12 is kept shielded by the capped needle guard 71.

The guarded winged needle assembly 21A is used in the same way as the guarded winged needle assembly 1A.

Figure 17A:
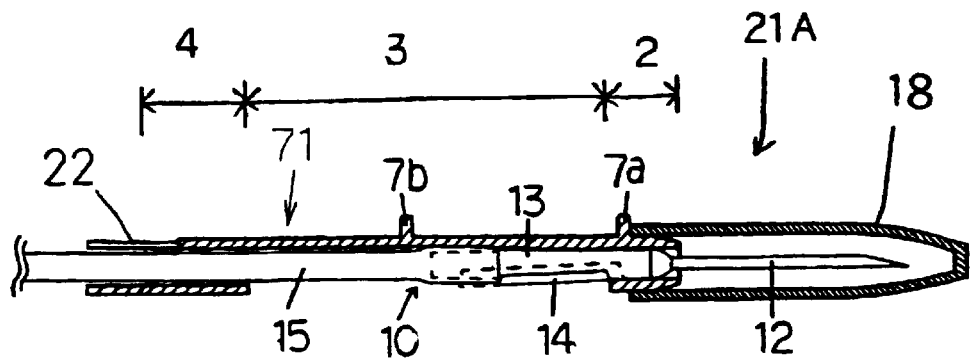
FIG. 17 is a cross-sectional view of the guarded winged needle assembly 21A with the capped needle guard 71 shown in the FIG. 16 apparatus attached to a winged needle assembly 10.
Figure 17B:
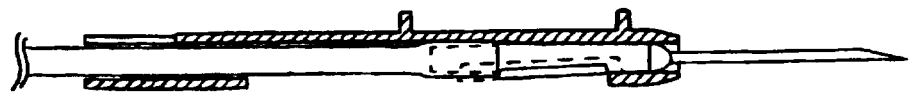

FIG. 18 is a perspective view showing usage of a guarded winged needle assembly 21A by drawing it as time series from FIGS. 18a to 18h. FIG. 17a corresponds to FIG. 18a, FIG. 17b to FIG. 18e, and FIG. 17d to FIG. 18h, respectively.

Figure 17C:
Figure 18A:
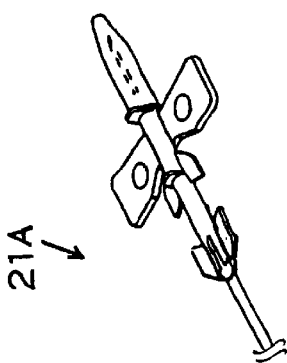
FIG. 18 is a perspective view showing usage of the guarded winged needle assembly 21A by showing it as time series from FIGS. 18a to 18h.
Figure 18B:
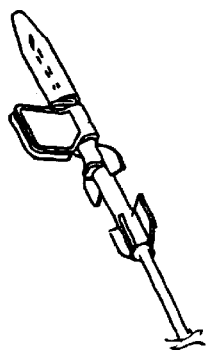
Figure 18C:
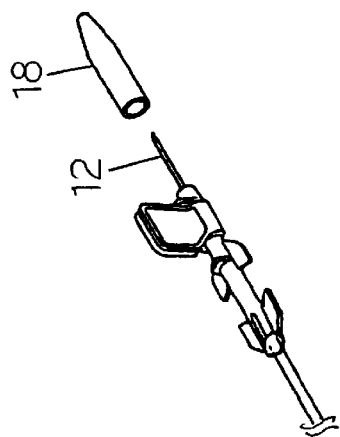
Figure 18D:
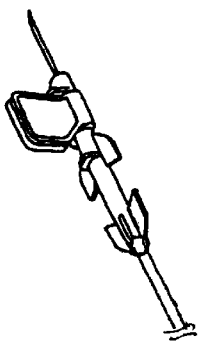
Figure 18E:
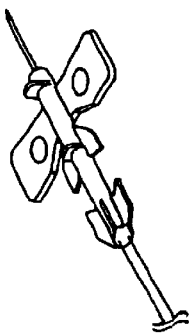
Figure 18F:
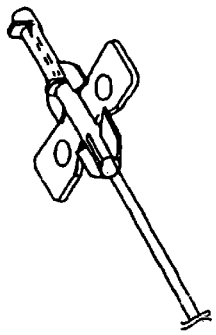

The relationships among FIG. 17c, FIG. 18f and FIG. 14 are substantially the same as the relationships among FIG. 12c, FIG. 13f and FIG. 14. Therefore, a drawing of a guarded winged needle assembly 21A corresponding to FIG. 14 is omitted.

Figure 17D:
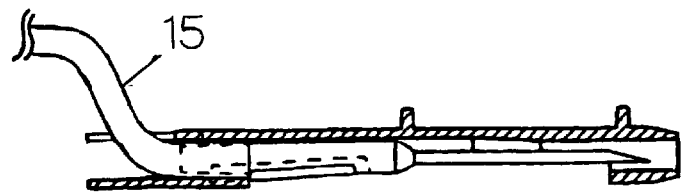
Figure 18G:
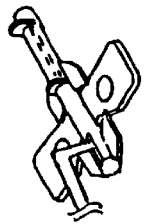
Figure 18H:
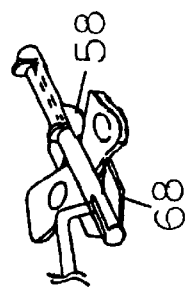

Similarly, the relationships among FIGS. 17d, 18h and 15 are substantially the same as the relationships among FIGS. 12d, 13h and 15. Therefore, a drawing of a guarded winged needle assembly 21A corresponding to FIG. 15 is omitted.

As shown in FIGS. 18a to 18h, the guarded winged needle assembly 21A is used by the operation of the above-mentioned ① through ⑧ procedures basically in the same manner as the guarded winged needle assembly 1A. The only difference between the guarded winged needle assembly 21A and its counterpart 1A is that with the former the detachably attached cap 18 is taken off, as shown in FIG. 18c, and expose the needle pin 12 of the winged needle assembly 10 from the capped needle guard 71.

(Alternative Embodiments of a Capped Needle Guard)

FIGS. 19 to 21 are views showing an alternative embodiment of this capped needle guard with stoppers of the present invention.

FIG. 19 is a schematic view of a preferable embodiment of the capped needle guard; FIG. 19a is an front perspective view of the capped needle guard 81; FIG. 19b is a rear perspective view of the same; FIG. 19c is a perspective view of the FIG. 19a apparatus, in a plane rotated by 180° with respect to the plane of FIG. 19a, and FIG. 19d is a perspective view of the FIG. 19b apparatus, in a plane rotated by 180° with respect to the plane of FIG. 19b.

The capped needle guard 81 is formed by attaching a cap 28 integrally molded via 28a (break-away part) with the top of the front portion 2 of the needle guard 1 instead of forming a detachable cap. A pair of ribs for manual gripping (not shown in figures) can be at least symmetrically formed on the outside surface of the cap 28 so that the cap 28 can be easily cut off.

A guarded winged needle assembly 31A can be set up in the same way as the capped needle guard 71 by attaching or mount the capped needle guard 81 to the winged needle assembly 10.

Figure 20A:
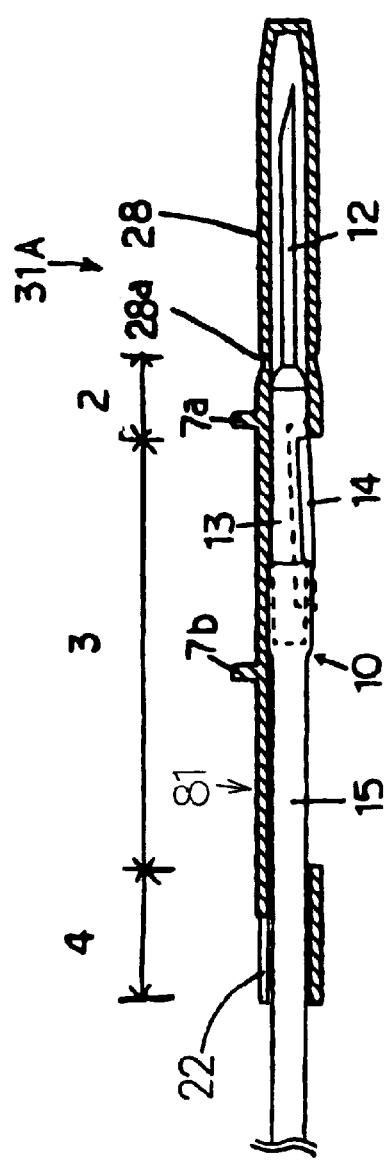
FIG. 20 is a cross-sectional view of an alternative embodiment of the guarded winged needle assembly 31A with the capped needle guard 81 attached to a winged needle assembly 10.

FIG. 20 is a cross-sectional view of the guarded winged needle assembly 31A shown in FIG. 19 with a capped needle guard 81 attached to the winged needle assembly 10. As shown in FIG. 20a, the winged needle assembly 10 and the capped needle guard 81 are fixed by attaching the front outside surface of the support 13 to the inside surface of the front portion 2 of the capped needle guard 81, as in FIG. 17. The needle pin 12 is kept shielded by the capped needle guard 81.

FIG. 21 is a perspective view showing usage of a guarded winged needle assembly 31A by showing it as time series. FIG. 20a corresponds to FIG. 21a, and FIG. 20b to FIG. 21e, respectively.

Figure 21D:
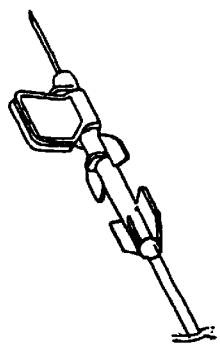
FIG. 21 is a perspective view showing usage of the guarded winged needle assembly 31A by showing it as time series from FIGS. 21a to 21h.
Figure 21C:
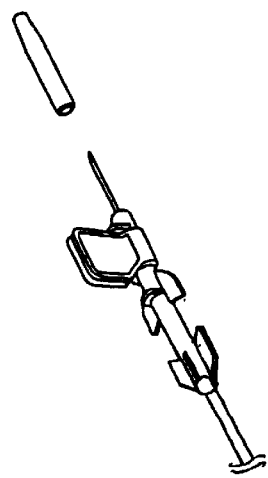
Figure 21B:
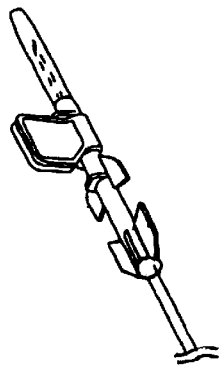
Figure 21A:
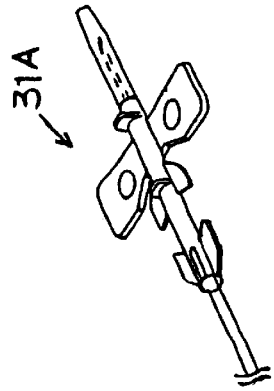

The guarded winged needle assembly 31A is used in the same way as the guarded winged needle assembly 21A, and is used by the above-mentioned ① through ⑧ procedures basically in the same manner as the guarded winged needle assembly 1A and others. The only difference between the guarded winged needle assembly 31A and its counterpart 21A is that with the former the cap 28 is cut off from the rim 28a(break-away part) as shown in FIG. 21c and become exposed from the capped needle guard 81.

(Fixing by Stoppers)

Here is a summary description of fixing a winged needle assembly by a capped needle guard with stoppers.

Figure 20B:

As shown in FIGS. 17c and 20b, the needle pin 12 of the winged needle assembly 10 is retracted in the capped needle assemblies 71 and 81 by sliding the winged needle assembly 10 toward the rear portion 4. Furthermore, the locking portion 58c locks the tip of the pair of wings 14 as shown in FIGS. 14 and 15.

Figure 21H:
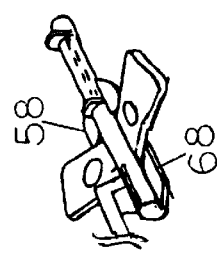
Figure 21G:
Figure 21F:
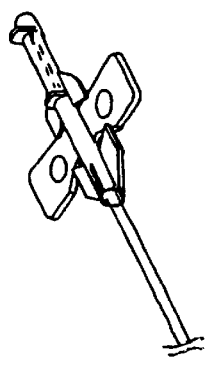
Figure 21E:
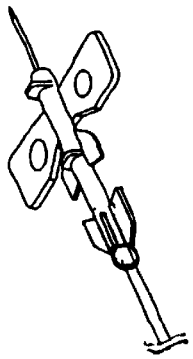

Preferably, as shown in FIG. 17d, the tube 15 is pulled backwards and lifted up. Then, as shown in FIGS. 18g and 21g, it is fixed in the groove 22 by passing the narrow portion 22b through the cutout portion 22'a shown in FIG. 11d.

Fixing the pair of wings of a winged needle assembly with stoppers and fixing the tube by the groove prevents the winged needle assembly 10 from accidental sliding toward the front portion 2 of the capped needle guards 71 and 81. By this way, the needle pin 12 of the winged needle assembly 10 is kept unexposed from the capped needle guards 71 and 81, thereby maintaining the winged needle assembly in a safe situation. Furthermore, as shown in FIGS. 18h and 21h, the pair of the wings 14 are crossed and locked between the stoppers 58 and 68 by folding them upwards. The needle pin 12 of the winged needle assembly 10 is not slid toward the front portion 2 of the capped needle guards 71 and 81, and is surely locked inside the capped needle guard 71 and 81 without being exposed.

(Protection Guard)

The needle guard of the present invention provides the aperture 5 for attaching the winged needle assembly connected to the tube at the back thereof.

For example, as shown in FIGS. 2d [3f] and FIGS. 12c[13f], when the needle of the winged needle assembly is retracted in the needle guard 1 after use, the needle and the support are exposed from the aperture. The needle with patient's blood on it preferably should not be exposed after use to avoid blood dripping.

Preferably, a protection guard should be attached to the aperture so that it will be completely covered.

FIG. 22 is a view showing the protection guard of the present invention for the needle guard and its attachment procedures.

Figure 22A:
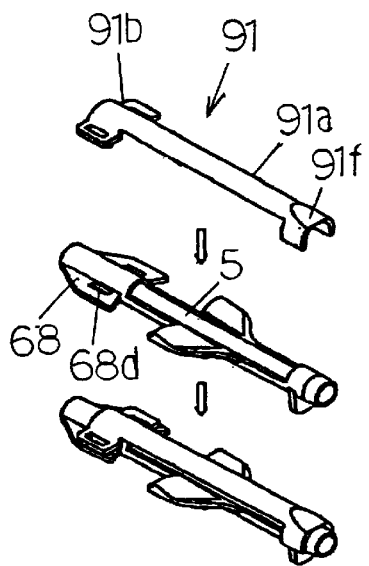
FIG. 22a is a bird's eye view showing how to attach the protection guard to this needle guard from the bottom of it.
Figure 22B:
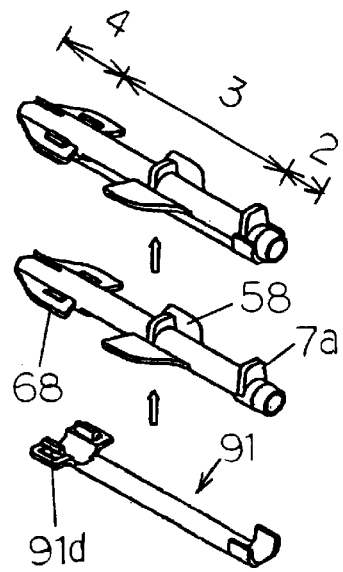
FIG. 22b is a worm's eye view of the FIG. 22a apparatus.

FIGS. 22a and 22b are schematic views showing a plate-type protection guard 91 and how to attach it to the needle guard for covering the whole aperture (needle and the support).

FIG. 22a is a bird's eye view of attaching the guard (plate-type protection guard 91) at the back of a protection guard, and FIG. 22b is a worm's eye view of the FIG. 22a apparatus.

Figure 22C:
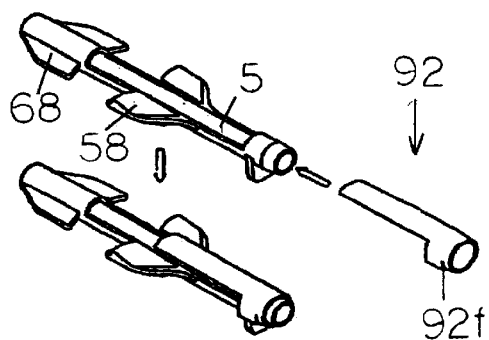
FIG. 22c is a bird's eye view showing how to attach a protection guard from the front end of the needle guard.
Figure 22D:
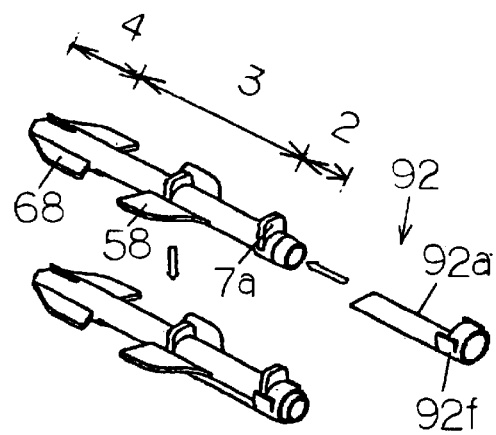
FIG. 22d is a worm's eye view of the FIG. 22c apparatus.

FIGS. 22c and 22d are schematic views showing the plate-type protection guard 92 which was formed to completely cover up the needle and how to attach it to the needle guard. FIG. 22c is a bird's eye view of attaching the guard (plated-type protection guard 91) at the bottom of the protection guard, and FIG. 22d is a worm's eye view of the FIG. 22c apparatus.

With respect to the case of the protection guard 91, a front attachment portion 91f and a rear attachment portions 91b are formed on both portions of the plate 91a. The plate 91a is curvedly formed so that it can cover the aperture 5, corresponding to the shape of the aperture 5 on the body 3 of the needle guard 1.

The front attachment portion 91f is half-circularly shaped so that it can be attached to the outside surface of the front portion 2.

The rear attachment portion 91b is formed as wing-shaped, corresponding to the shape of the wing-shaped stoppers 68 on the rear portion 4 of the needle guard 1, and locking portions 91d are formed, corresponding to the locking portions 68d on the stoppers 68. This means that there are two protruding locking portions 91d and two grooved locking portions 68d on the stoppers 68 corresponding to said lacking portions 91d. The relationship between the protrusions and grooves of the locking portions 91d and 68d can be reversed.

The shapes of the plate 91a, the front attachment portion 91f and the rear attachment portions 91b are not limited to the ones described in the drawings. They can be any shapes or design-changed as long as they can cover the aperture 5, corresponding to the shape of the needle guard 10. For example, the rear attachment portions 91b of the needle guard 1 shown in FIG. 10 are wing-shaped, and the ones shown in FIG. 1 are shaped as circular or cylinder to be attached to the outside surface of the rear portion 4.

In the case of the protection guard 92, a front attachment portion 92f is attached to the front portion of the plate 92a. The plate 92a is curvedly formed corresponding to the shape of the aperture 5 on the body 3 of the needle guard 1 so that it can cover the aperture 5 thereby preventing the needle from exposing from the aperture.

The front attachment portion 92f is formed cylindrical, corresponding to the outside surface of the front portion 2 so that it can be touched to the outside surface of it.

The shapes of the plate 92a and the front attachment portion 91f are not limited to the ones described in the drawings. They can be any shapes or design-changed as long as needles are not exposed from the aperture 5, corresponding to the shape of the needle guard 1.

(Materials)

The materials used for the needle guard, capped needle guard, wings, stoppers, and protection guard of the present invention, even though they are not intended to be limited to the followings, should be preferably semi-rigid or rigid resins such as polypropylene, polyethylene, polyvinyl chloride, polycarbonate, polymethyl methacrylate, polyurethane, polyamide, polystyrene, polyethylene terephthalate, polyphenylene sulfide, polyether ether ketone, polyacetal and others.

(Advantageous Effects of the invention)

Here are the advantageous effects or the technical merits of the needle guard, capped needle guard, and guarded winged needle assembly of the present invention.

(Effects of the Needle Guard with Locking Grooves)

① The needle guard 1, guarded needle winged assemblies 1A, 21A, 31A, and capped needle guards 71 and 81 comprise the groove 22 on the top of the rear portion 4 and other projecting portions 23a and 23b facing to each other at the back of the groove 22. The tube 15, which is attached to the winged needle assembly 10, and which is connected to the rear portion 4 of guarded winged needle assemblies 1A, 21A and 31A, is pinched and fixed into the groove 22 after passing through the projecting portions 23a and 23b. Its easy and secure fixing prevents the needle pin 12 from sliding and exposing front end of the guard.

② This invention
(a) makes it possible to fix the winged needle assembly 10 with the needle guard 1 and capped needle guards 71 and 81 when setting them up,
(b) makes it possible to easily expose the needle pin 12 from the needle guard 1 and capped needle guards 71 and 81 by uncapping the needle cap 16 or caps 18 and 28 during use, and
(c) makes it possible to securely fix the winged needle assembly 10 and avoid moving toward the front portion 2 of the needle guard 1 and capped needle guards 71 and 81 The tube 15 of the winged needle assembly 10 is securely fixed between projecting portions 23a and 23b facing to each other at the back of the groove 22 from the rear portion 4 to the projecting portion 7c of the needle guard 1 and capped needle guards 71 and 81, and therefore, accidental exposure of the needle pin 12 can be prevented. The risk of accidental needle sticks by medical workers and waste disposal workers will be reduced to minimum or eliminated.

(Effects of a Needle Guard with Stoppers)

① This needle guard with stoppers of the present invention comprises stoppers 58, thick portions 58b, and locking portions 58c at the back of the thick portions 58b. When retracting the winged needle assembly 10 into the needle guard or capped needle guard, secure and strong lock of the wing 14 with the locking portions 58c prevents the needle pin 12 from exposing outside.

② After use of needle guard with stoppers, the second stoppers 68 together with the stoppers 58 make it possible to firmly cross-fix and lock the wings 14 between the first stoppers 58 and the second 68 by folding the wings 14 upwards when retracting the winged needle assembly into the needle guard or capped needle guard. Secure lock of a winged needle assembly prevents the needle pin 12 from exposing outside.

③ In this needle guard with stoppers, the groove 22 at the rear portion 4 pinches and fixes the tube 15 of the winged needle assembly 10 therein. Blood remaining in the tube 15 does not drip out of the needle pin 12 since the flow line in the tube 15 is blocked. In this way, both blood dripping remaining in the winged needle assembly 10 and exposure of the needle pin 12 can be prevented.

④ In this needle guard with stoppers, the cutout portion 22'a and the groove 22 are formed on the top of the rear portion 4. The narrow portion 22b is formed between the cutout portion 22'a and the groove 22, and the horn portion 22c is formed in the narrow portion 22b. The tube 15 at the back of the rear portion 4 of the guarded winged needle assembly which is attached to the winged needle assembly 10 is pulled backward to be pinched and fixed in the groove 22. Furthermore, the horn portion 22c in the narrow portion 22b blocks the tube from coming off of the narrow portion 22b and prevents the needle pin 12 from exposing outside.

Here are the common effects of the needle guard with locking grooves and a needle guard with stoppers.

① Mere linear sliding of the winged needle assembly 10 toward both of the front directions of the needle guard 1 and capped needle guards 71 and 81 allows easy shielding of the needle, securing very good operationality.

② The capped needle guard 81 makes it possible to both protect the needle and slide the needle guard altogether at the same time, and therefore, the number of parts is lessened and operationality is better.

③ Projecting portions 7a, 7b, and 7c for manual gripping on topwalls of the needle guard 1 and capped needle guards 71, and 81 make it easy to fix the needle guard during work and easy to slide the winged needle assembly 10.

What is claimed is:

1. An elongated cylindrical needle guard for attaching and protecting a medical needle to which a tube is connected, said needle gaurd comprising:
   a cylindrical body consisting of a front portion, a body and a rear portion;
   an aperture at the bottom of the body;
   at least two or more projecting portions on the top wall of the cylindrical body from the front portion to the rear portion;
   a slit at the bottom of the rear portion along a longitudinal direction of said needle guard;
   a groove for fixing the tube on the top of the rear portion; and
   projecting portions facing to each other at the back of said groove.

2. A needle guard according to claim 1, wherein a cutout portion in said projecting portion is formed in upwardly-widened tapered shape.

3. A capped needle guard, wherein a cap is detachably attached to the front portion of said needle guard according to claim 1.

4. A capped needle guard, wherein a cap is integrally molded via a rim with the front portion of said needle guard according to claim 1.

5. A guarded winged needle assembly, wherein said needle guard according to claim 1 or said capped needle guard according to claim 2 or claim 3 is attached to a winged needle assembly.

6. A guarded winged needle assembly, comprising:
   a winged needle assembly, in which a needle pin is attached to the front portion of a support, to which a pair of wings is attached to sides of the support, to which a needle cap is attached on the front outside surface of the support, and to which a tube is connected on the rear outside surface of the support; and
   a needle guard according to claim 1 or claim 2 which is slidably mounted on said winged needle assembly; wherein:
      in a situation that said winged needle assembly is attached and retracted to said needle guard through an aperture and a slit;
      the outside surface of the needle cap is attached to the inside surface of the front portion;
   said winged needle assembly is fixed to said needle guard;
   the needle pin is shielded in the needle cap;
   the needle pin of said winged needle assembly is exposed by uncapping the needle cap;
   the needle pin of said winged needle assembly is retracted into said needle guard by sliding said winged needle assembly toward the rear portion of said needle guard; and
   the tube is fixed into a groove through projecting portions facing to each other by backwardly pulling it and lifting it up; thereby
   said winged needle assembly being kept not to slide toward the front portion of said needle guard and the needle pin of said winged needle assembly being kept not to be exposed from said needle guard.

7. A guarded winged needle assembly, comprising:
   a winged needle assembly, in which a needle pin is attached to a front portion of a support, to which a pair of wings is attached to both sides of the support, and to which a tube is connected to the rear outside surface of the support; and
   a capped needle guard according to claim 3 or claim 4 which is slidably mounted on said winged needle assembly; wherein:
      in a situation that said winged needle assembly is attached and retracted to said capped needle guard through an aperture and a slit;
      the front outside surface of the support is attached to the inside surface of the front portion of said capped needle guard;
   said winged needle assembly is fixed to said capped needle guard;
   the needle pin is shielded in said capped needle guard;
   the needle pin is exposed by uncapping said capped needle guard;
   the needle pin of said winged needle assembly is retracted into said capped needle guard by sliding said winged needle assembly toward the rear portion of said capped needle guard; and
   the tube is fixed into a groove through projecting portions facing to each other by backwardly pulling it and lifting it up; thereby
   said winged needle assembly being kept not to slide toward the front portion of said capped needle guard and the needle pin being kept not to be exposed from said capped needle guard.

8. An elongated cylindrical needle guard for attaching and protecting a medical needle to which a tube is connected, comprising:
   a cylindrical body consisting of a front portion, a body and a rear portion;
   an aperture at the bottom of the body;
   a pair of stoppers both sides of the body;
   having an area of increased thickness each of the stoppers; and
   locking portions on the back of each of the thick portions for locking wings of a winged needle assembly.

9. A needle guard according to claim 8, further comprising a pair of second stoppers on sides of the rear portion.

10. A needle guard according to claim 8, further comprising a groove for fixing the tube on the top wall of the rear portion.

11. A needle guard according to claim 10, further comprising:
   a cutout portion at the back of the groove; and
   a narrow portion between the groove and the cutout portion.

12. A needle guard according to claim 8, further comprising:
   projecting portions on the top wall from the front portion to the body; and
   a slit at the bottom of the rear portion along a longitudinal direction of said needle guard.

13. A capped needle guard, wherein a cap is detachably attached at the front portion of said needle guard according to claim 8.

14. A capped needle guard, wherein a cap is integrally molded via a rim with the front portion of said needle guard according to claim 8.

15. A guarded winged needle assembly, where in said needle guard according to any one of claims 8 to 12 or said capped needle guard according to claim 13 or claim 14 is mounted on the winged needle assembly.

16. A guarded winged needle assembly, comprising:
a winged needle assembly, in which a needle pin is attached to the front portion of a support, to which a pair of wings is attached on both sides of the support, to which a needle cap is attached the front outside surface of the support, and to which a tube is connected on the rear outside surface of the support; and
a needle guard according to any one of claims 8 to 12 which is slidably mounted on said winged needle assembly; wherein:
in a situation that said winged needle assembly is attached and retracted to said needle guard through an aperture and a slit;
the outside surface of the needle cap is attached to the inside surface of the front portion;
said winged needle assembly is fixed to said needle guard;
the needle pin is shielded in the needle cap;
the needle pin of said winged needle assembly is exposed by uncapping the needle cap;
the needle pin of said winged needle assembly is retraced into said needle guard by sliding said winged needle assembly toward the rear portion of said needle guard; and
locking portions are locked to tips of the wings; thereby
said winged needle assembly being kept not to slide toward the front portion of said needle guard and the needle pin of said winged needle assembly being kept not to be exposed from said needle guard.

17. A guarded winged needle assembly, comprising:
a winged needle assembly, in which a needle pin is attached to the front portion of a support, to which a pair of wings is attached on both sides of the support, and to which a tube is connected to the rear outside surface of the support; and
a capped needle guard according to claim 13 or claim 14 which is slidably mounted on said winged needle assembly; wherein:
in a situation that said winged needle assembly is attached and retracted to said capped needle guard through an aperture and a slit;
the front outside surface of the support is attached to the inside surface of the front portion of said capped needle guard;
said winged needle assembly is fixed to said capped needle guard;
the needle pin is shielded in said capped needle guard;
the needle pin is exposed by uncapping said capped needle guard;
the needle pin of said winged needle assembly is retracted into said capped needle guard by sliding said winged needle assembly toward the rear portion of said capped needle guard; and
locking portions are locked to tips of the wings; thereby
said winged needle assembly being kept not to slide toward the front portion of said capped needle guard and the needle pin of said winged needle assembly being kept not to be exposed from said capped needle guard.

18. A guarded winged needle assembly according to claim 16, wherein the pair of wings are crosswardly locked between the stoppers and the second stoppers by folding the wings upwards.

19. A guarded winged needle assembly according to claim 16, wherein the tube are fixed in the groove from the cutout portion to the narrow portion by backwardly pulling the tube and lifting it up.

20. A protection guard for the needle guard according to claim 1 or claim 8, comprising:
a front attachment portion and a rear portion attachment portion on both sides of plate, respectively,
wherein said front attachment portion and said rear portion attachment portion are attached to the front portion and the rear portion of said needle guard, respectively; thereby
the aperture at the body of said needle guard being covered to cover the needle and the support of said winged needle assembly.

21. A protection guard for a needle guard according to claim 1 or claim 8, comprising:
a front attachment portion on a plate; and
said front attachment portion is attached to the front portion of said needle guard,
wherein a portion of the aperture at the body of said needle guard is covered by the plate so that at least the needle is not exposed.

22. A guarded winged needle assembly according to claim 17, wherein the pair of wings are crosswardly locked between the stoppers and the second stoppers by folding the wings upwards.

23. A guarded winged needle assembly according to claim 17, wherein the tube are fixed in the groove from the cutout portion to the narrow portion by backwardly pulling the tube and lifting it up.

24. A guarded winged needle assembly according to claim 18, wherein the tube are fixed in the groove from the cutout portion to the narrow portion by backwardly pulling the tube and lifting it up.

25. A guarded winged needle assembly according to claim 22, wherein the tube are fixed in the groove from the cutout portion to the narrow portion by backwardly pulling the tube and lifting it up.

* * * * *